US006444671B1

(12) United States Patent
Gaudino

(10) Patent No.: US 6,444,671 B1
(45) Date of Patent: Sep. 3, 2002

(54) CYCLIC AMP-SPECIFIC PHOSPHODIESTERASE INHIBITORS

(75) Inventor: John J. Gaudino, Boulder, CO (US)

(73) Assignee: ICOS Corporation, Bothell, WA (US)

( * ) Notice: Subject to any disclaimer, the term of this patent is extended or adjusted under 35 U.S.C. 154(b) by 0 days.

(21) Appl. No.: 10/002,867

(22) Filed: Nov. 15, 2001

Related U.S. Application Data

(62) Division of application No. 09/737,987, filed on Dec. 15, 2000, now Pat. No. 6,362,213.
(60) Provisional application No. 60/173,019, filed on Dec. 23, 1999.

(51) Int. Cl.$^7$ .................. C07D 413/14; A61K 31/5377; A61P 19/00
(52) U.S. Cl. .............................. 514/234.5; 514/254.06; 544/96; 544/371; 544/372
(58) Field of Search .................. 514/234.5, 254.06; 544/96, 371, 372

(56) References Cited

U.S. PATENT DOCUMENTS

| | | | |
|---|---|---|---|
| 5,459,158 A | 10/1995 | Moore et al. | 514/406 |
| 5,665,754 A | 9/1997 | Feldman et al. | 514/397 |
| 5,965,582 A | 10/1999 | Labaut et al. | 514/338 |
| 5,998,428 A | 12/1999 | Barnette et al. | 514/285 |
| 6,040,329 A | 3/2000 | Marfat et al. | 514/405 |
| 6,162,819 A | 12/2000 | Schindler et al. | 514/405 |

FOREIGN PATENT DOCUMENTS

| | | | |
|---|---|---|---|
| WO | WO 97/42174 | 11/1997 | C07D/231/56 |
| WO | WO 97/49702 | 12/1997 | C07D/403/04 |
| WO | WO 98/09961 | 3/1998 | C07D/401/12 |
| WO | WO 99/23706 | 5/1999 | H01L/31/048 |

OTHER PUBLICATIONS

J.E. Schultz et al., *Naunyn–Schmiedeberg's Arch Pharmacol*, 333, pp. 23–30 (1986).
Z. Ma et al., *Tetrahedron: Asymmetry*, vol. 8, No. 6, pp. 883–887 (1997).
A. Robichaud et al., *Neuropharmacology*, 38, pp. 289–297 (1999).
R.A. Allen et al., *Biochemical Pharmacology*, vol. 57, pp. 1375–1382 (1999).
J. Beavo et al., "Cyclic nucleotide phosphodiesterases: Structure, regulation and drug action," Wiley and Sons, Chichester, pp. 3–14 (1990).
T.J. Torphy et al., *Drug News and Perspectives*, 6, pp. 203–214 (1993).
M.A. Giembycz et al., *Clin. Exp. Allergy*, 22, pp. 337–344 (1992).
J. Semmler et al., *Int. J. Immunopharmacol.*, 15, pp. 409–413 (1993).
K.L. Molnar–Kimber et al., *Mediators of Inflammation*, 1, pp. 411–417 (1992).
M.W. Verghese et al., *J. Mol. Cell. Cardiiol.*, 21 (Suppl. 2), S61 (1989).
C.P. Nielson et al., *J. Allergy Immunol.*, 86, pp. 801–808 (1990).
P.T. Peachell et al., *J. Immunol.*, 148, pp. 2503–2510 (1992).
G. Dent et al., *J. Pharmacol.*, 103, pp. 1339–1346 (1991).
S.A. Robicsek et al., *Biochem. Pharmacol.*, 42, pp. 869–877 (1991).
H.S. Dhillon et a., *J. Neurotrauma*, 12, pp. 1035–1043 (1995).
N. Suttorp et al., *J. Clin. Invest.*, 91, pp. 1421–1428 (1993).
M.R. Bristow et al., *Circulation*, 97, pp. 1340–1341 (1998).
G. Poli et al., *Proc. Natl. Acad. Sci. USA*, 87, pp. 782–785 (1990).
P. Orosz et al., *J. Exp. Med.*, 177, pp. 1391–1398 (1993).
M. Mentz et al., *Blood*, 88, pp. 2172–2182 (1996).
S. Takeda et al., *Kidney Int.*, 37, p. 362 (1990).
D. Chabardea et al., *Kidney Int.*, 35, p. 494 (1989).
C.D. Nicholson, *Psychopharmacology*, 101, p. 147 (1990).
F. Eckmann et al., *Curr. Ther. Res.*, 43, p 291 (1988).
A. Klodzinska et al., *Neuropharmacology*, 38, p. 1831 (1991).
H. Kato et al., *Eur. J. Pharmacol.*, 272, p. 107 (1995).
G. Gardos et al., *J. Clin. Pharmocol.*, 16, p. 304 (1976).
I. Shoulson et al., *Neurology*, 25, p. 722 (1975).
T. Hayakawa et al., *Clin. Exp. Pharmacol. Physiol.*, 26, p. 421 (1999).
R.D. Porsolt et al., *Eur. J. Pharmacol.*, 47, p. 379 (1978).
R.D. Porsolt et al., *Eur. J. Pharmacol.*, 57, p. 431 (1979).
L. Steru, *Psychopharmacology*, 85, p. 376 (1985).
M. Takahashi, *J. Neuroscience*, 19, p. 610 (1999).
D. Pinsky et al., *J. Clin. Invest.*, 92, pp. 2994–3002 (1993).
*Antidepressants: neurochemical, behavioral and clinical prospectives*, Enna, Malick, and Richelson, eds., Raven Press, pp. 121–139 (1981).

*Primary Examiner*—Joseph K. McKane
*Assistant Examiner*—Kamal Saeed
(74) *Attorney, Agent, or Firm*—Marshall, Gerstein & Borun.

(57) ABSTRACT

Novel compounds that are potent and selective inhibitors of PDE4, as well as methods of making the same, are disclosed. Use of the compounds in the treatment of inflammatory diseases and other diseases involving elevated levels of cytokines, as well as central nervous system (CNS) disorders, also is disclosed.

34 Claims, No Drawings

CYCLIC AMP-SPECIFIC PHOSPHODIESTERASE INHIBITORS

CROSS-REFERENCE TO RELATED APPLICATIONS

This application is a divisional of application Ser. No. 09/737,987, filed Dec. 15, 2000, now U.S. Pat. No. 6,362,213, which claims benefit of provisional application Ser. No. 60/173,019, filed Dec. 23, 1999.

FIELD OF INVENTION

The present invention relates to a series of compounds that are potent and selective inhibitors of cyclic adenosine 3',5'-monophosphate specific phosphodiesterase (cAMP specific PDE). In particular, the present invention relates to a series of novel indazole compounds that are useful for inhibiting the function of cAMP specific PDE, in particular, PDE4, as well as methods of making the same, pharmaceutical compositions containing the same, and their use as therapeutic agents, for example, in treating inflammatory diseases and other diseases involving elevated levels of cytokines and proinflammatory mediators.

BACKGROUND OF THE INVENTION

Chronic inflammation is a multi-factorial disease complication characterized by activation of multiple types of inflammatory cells, particularly cells of lymphoid lineage (including T lymphocytes) and myeloid lineage (including granulocytes, macrophages, and monocytes). Proinflammatory mediators, including cytokines, such as tumor necrosis factor (TNF) and interleukin-1 (IL-1), are produced by these activated cells. Accordingly, an agent that suppresses the activation of these cells, or their production of proinflammatory cytokines, would be useful in the therapeutic treatment of inflammatory diseases and other diseases involving elevated levels of cytokines.

Cyclic adenosine monophosphate (cAMP) is a second messenger that mediates the biologic responses of cells to a wide range of extracellular stimuli. When the appropriate agonist binds to specific cell surface receptors, adenylate cyclase is activated to convert adenosine triphosphate (ATP) to cAMP. It is theorized that the agonist induced actions of cAMP within the cell are mediated predominately by the action of cAMP-dependent protein kinases. The intracellular actions of cAMP are terminated by either a transport of the nucleotide to the outside of the cell, or by enzymatic cleavage by cyclic nucleotide phosphodiesterases (PDEs), which hydrolyze the 3'-phosphodiester bond to form 5'-adenosine monophosphate (51-AMP). 5'-AMP is an inactive metabolite. The structures of cAMP and 5'-AMP are illustrated below.

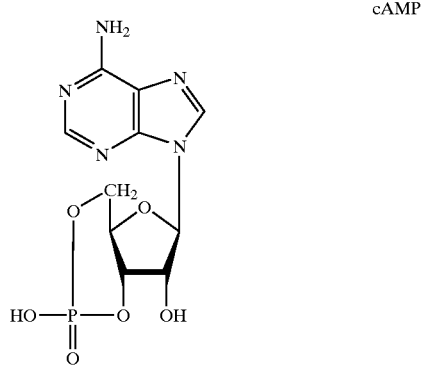

cAMP

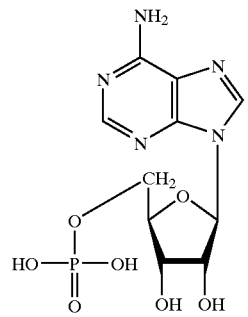

5'-AMP

Elevated levels of cAMP in human myeloid and lymphoid lineage cells are associated with the suppression of cell activation. The intracellular enzyme family of PDEs, therefore, regulates the level of cAMP in cells. PDE4 is a predominant PDE isotype in these cells, and is a manor contributor to cAMP degradation. Accordingly, the inhibition of PDE function would prevent the conversion of cAMP to the inactive metabolite 5'-AMP and, consequently, maintain higher cAMP levels, and, accordingly, suppress cell activation (see Beavo et al., "Cyclic Nucleotide Phosphodiesterases: Structure, Regulation and Drug Action," Wiley and Sons, Chichester, pp. 3–14 (1990)); Torphy et al., *Drug News and Perspectives*, 6, pp. 203–214 (1993); Giembycz et al., *Clin. Exp. Allergy*, 22, pp. 337–344 (1992)).

In particular, PDE4 inhibitors, such as rolipram, have been shown to inhibit production of TNFα and partially inhibit IL-1β release by monocytes (see Semmler et al., *Int. J. Immunopharmacol.*, 15, pp. 409–413 (1993); Molnar-Kimber et al., Mediators of Inflammation, 1, pp. 411–417 (1992)). PDE4 inhibitors also have been shown to inhibit the production of superoxide radicals from human polymorphonuclear leukocytes (see Verghese et al., *J. Mol. Cell. Cardiol.*, 21 (Suppl. 2), S61 (1989); Nielson et al.,*J. Allergy Immunol.*, 86, pp. 801–808 (1990)); to inhibit the release of vasoactive amines and prostanoids from human basophils (see Peachell et al., *J. Immunol.*, 148, pp. 2503–2510 (1992)); to inhibit respiratory bursts in eosinophils (see Dent et al., *J. Pharmacol.*, 103, pp. 1339–1346 (1991)); and to inhibit the activation of human T-lymphocytes (see Robicsek et al., *Biochem. Pharmacol.*, 42, pp. 869–877 (1991)).

Inflammatory cell activation and excessive or unregulated cytokine (e.g., TNFα and IL-1β) production are implicated in allergic, autoimmune, and inflammatory diseases and disorders, such as rheumatoid arthritis, osteoarthritis, qouty arthritis, spondylitis, thyroid associated ochthalmopathy, Behcet's disease, sepsis, septic shock, endotoxic shock, gram negative sepsis, gram positive sepsis, toxic shock syndrome, asthma, chronic bronchitis, adult respiratory distress syndrome, chronic pulmonary inflammatory disease, such as chronic obstructive pulmonary disease, silicosis, pulmonary sarcoidosis, reperfusion injury of the myocardium, brain, and extremities, fibrosis, cystic fibrosis, keloid formation, scar formation, atherosclerosis, transplant rejection disorders, such as graft vs. host reaction and allograft rejection, chronic glomerulonephritis, lupus, inflammatory bowel disease, such as Crohn's disease and ulcerative colitis, proliferative lymphocyte diseases, such as leukemia, and inflammatory dermatoses, such as atopic dermatitis, psoriasis, and urticaria.

Other conditions characterized by elevated cytokine levels include brain injury due to moderate trauma (see Dhillon et al., *J. Neurotrauma*, 12, pp. 1035–1043 (1995); Suttorp et al., *J. Clin. Invest.*, 91, pp. 1421–1428 (1993)), cardiomyopathies, such as congestive heart failure (see Bristow et al., *Circulation*, 97, pp. 1340–1341 (1998)), cachexia, cachexia secondary to infection or malignancy, cachexia secondary to acquired immune deficiency syndrome (AIDS), ARC (AIDS related complex), fever myalgias due to infection, cerebral malaria, osteoporosis and bone resorption diseases, keloid formation, scar tissue formation, and pyrexia.

In particular, TNFα has been identified as having a role with respect to human acquired immune deficiency syndrome (AIDS). AIDS results from the infection of T-lymphocytes with Human Immunodeficiency Virus (HIV). Although HIV also infects and is maintained in myeloid lineage cells, TNF has been shown to upregulate HIV infection in T-lymphocytic and monocytic cells (see Poli et al., *Proc. Natl. Acad. Sci. USA*, 87, pp. 782–785 (1990)).

Several properties of TNFα, such as stimulation of collagenases, stimulation of angiogenesis in vivo, stimulation of bone resorption, and an ability to increase the adherence of tumor cells to endothelium, are consistent with a role for TNF in the development and metastatic spread of cancer in the host. TNFα recently has been directly implicated in the promotion of growth and metastasis of tumor cells (see Orosz et al., *J. Exp. Med.*, 177, pp. 1391–1398 (1993)).

PDE4 has a wide tissue distribution. There are at least four genes for PDE4 of which multiple transcripts from any given gene can yield several different proteins that share identical catalytic sites. The amino acid identity between the four possible catalytic sites is greater than 85%. Their shared sensitivity to inhibitors and their kinetic similarity reflect the functional aspect of this level of amino acid identity. It is theorized that the role of these alternatively expressed PDE4 proteins allows a mechanism by which a cell can differentially localize these enzymes intracellularly and/or regulate the catalytic efficiency via post translational modification. Any given cell type that expresses the PDE4 enzyme typically expresses more than one of the four possible genes encoding these proteins.

Investigators have shown considerable interest in the use of PDE4 inhibitors as anti-inflammatory agents. Early evidence indicates that PDE4 inhibition has beneficial effects on a variety of inflammatory cells such as monocytes, macrophages, T-cells of the Th-1 lineage, and granulocytes. The synthesis and/or release of many proinflammatory mediators, such as cytokines, lipid mediators, superoxide, and biogenic amines, such as histamine, have been attenuated in these cells by the action of PDE4 inhibitors. The PDE4 inhibitors also affect other cellular functions including T-cell proliferation, granulocyte transmigration in response to chemotoxic substances, and integrity of endothelial cell junctions within the vasculature.

The design, synthesis, and screening of various PDE4 inhibitors have been reported. Methylxanthines, such as caffeine and theophylline, were the first PDE inhibitors discovered, but these compounds are nonselective with respect to which PDE is inhibited. The drug rolipram, an antidepressant agent, was one of the first reported specific PDE4 inhibitors. Rolipram, having the following structural formula, has a reported 50% Inhibitory Concentration ($IC_{50}$) of about 200 nM (nanomolar) with respect to inhibiting recombinant human PDE4.

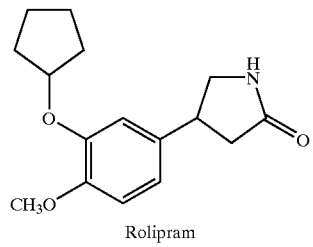

Rolipram

Investigators have continued to search for PDE4 inhibitors that are more selective with respect to inhibiting PDE4, that have a lower $IC_{50}$ than rolipram, and that avoid the undesirable central nervous system (CNS) side effects, such as retching, vomiting, and sedation, associated with the administration of rolipram. one class of compounds is disclosed in Feldman et al. U.S. Pat. No. 5,665,754. The compounds disclosed therein are substituted pyrrolidines having a structure similar to rolipram. One particular compound, having structural formula (I), has an $IC_{50}$ with respect to human recombinant PDE4 of about 2 nM. Inasmuch as a favorable separation of emetic side effect from efficacy was observed, these compounds did not exhibit a reduction in undesirable CNS effects.

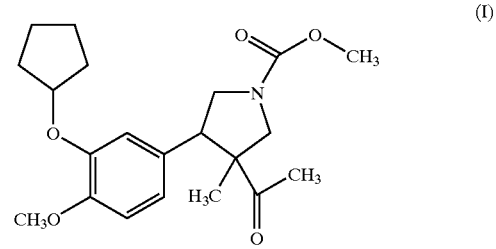

(I)

In addition, several companies are now undertaking clinical trials of other PDE4 inhibitars. However, problems relating to efficacy and adverse side effects, such as emesis and central nervous system disturbances, remain unsolved.

Accordingly, compounds that selectively inhibit PDE4, and that reduce or eliminate the adverse CNS side effects associated with prior PDE4 inhibitors, would be useful in the treatment of allergic and inflammatory diseases, and other diseases associated with excessive or unregulated production of cytokines, such as TNF. In addition, selective PDE4 inhibitors would be useful in the treatment of diseases that are associated with elevated cAMP levels or PDE4 function in a particular target tissue.

SUMMARY OF THE INVENTION

The present invention is directed to potent and selective PDE4 inhibitors useful in treatment of diseases and conditions where inhibition of PDE4 activity is considered beneficial. The present PDE4 inhibitors unexpectedly reduce or eliminate the adverse CNS side effects associated with prior PDE4 inhibitors.

In particular, the present invention is directed to compounds having the structural formula (II):

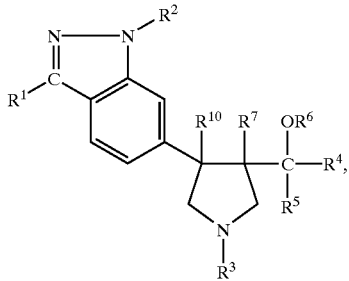

(II)

wherein $R^1$ is hydrogen, lower alkyl, bridged alkyl (e.g., norbornyl), aryl (e.g., phenyl), heteroaryl, cycloalkyl, a 5- or 6-membered saturated heterocycle (e.g., 3-tetrahydrofuryl), $C_{1-3}$alkylenecycloalkyl (e.g., cyclopentylmethyl), aryl- or heteroaryl-substituted propargyl (e.g., —$CH_2C \equiv C$—$C_6H_5$), aryl- or heteroaryl-substituted allyl (e.g., —$CH_2CH = CH$—$C_6H_5$), or halocycloalkyl (e.g., fluorocyclopentyl);

$R^2$ is hydrogen, lower alkyl, bridged alkyl, cycloalkyl, haloalkyl, halocycloalkyl, $C_{1-3}$alkylenecycloalkyl, a 5- or 6-membered saturated heterocycle, aryl, heteroaryl, aralkyl, alkaryl, heteroaralkyl, or heteroalkaryl;

$R^3$ is $C(=O)$ $OR^7$, $C(=O)$ $R^7$, $C(=NH)NR^8R^9$, $C(=O)$—$NR^8R^9$, lower alkyl, bridged alkyl, cycloalkyl, haloalkyl, halocycloalkyl, $C_{1-3}$alkylenecycloalkyl, a 5- or 6-membered saturated heterocycle, aryl, heteroaryl, heteroaryl$SO_2$, aralkyl, alkaryl, heteroaralkyl, heteroalkaryl, $C_{1-3}$alkyleneC$(=O)OR^7$, $C(=O)C_{1-3}$alklene-C$(=O)OR^7$, $C_{1-3}$alkyleneheteroaryl, $C(=O)C(=O)OR^7$, $C(=O)C_{1-3}$alkyleneC$(=O)OR^7$, $C(=O)C_{1-3}$alkyleneNH$(C=O)OR^7$, $C(=O)C_{1-3}$alkyleneNH$_2$, or NHC$(=O)OR^7$;

$R^4$ is hydrogen, lower alkyl, haloalkyl, cycloalkyl, or aryl;

$R^5$ is hydrogen, lower alkyl, alkynyl, haloalkyl, cycloalkyl, or aryl;

$R^6$ is hydrogen, lower alkyl, or $C(=O)R^7$;

$R^7$ is lower alkyl, branched or unbranched, or aryl, either optionally substituted with one or more of $OR^8$, $NR^8R^9$, or $SR^8$;

$R^8$ and $R^9$, same or different, are selected from the group consisting of hydrogen, lower alkyl, cycloalkyl, aryl, heteroaryl, alkaryl, heteroaralkyl, heteroalkaryl, and aralkyl, or $R^8$ and $R^9$ together form a 4-membered to 7-membered ring;

$R^{10}$ is hydrogen, alkyl, haloalkyl, cycloalkyl, aryl, $C(=O)$alkyl, $C(=O)$cycloalkyl, $C(=O)$aryl, $C(=O)$Oalkyl, $C(=O)$Ocycloalkyl, $C(=O)$aryl, $CH_2OH$, $CH_2O$alkyl, CHO, CN, $NO_2$, or $SO_2R^{11}$; and $R^{11}$ is alkyl, cycloalkyl, trifluoromethyl, aryl, aralkyl, or $NR^8R^9$.

The present invention also is directed to pharmaceutical compositions containing one or more of the compounds of structural formula (II), to use of the compounds and compositions containing the compounds in the treatment of a disease or disorder, and to methods of preparing compounds and intermediates involved in the synthesis of the compounds of structural formula (II).

The present invention also is directed to methods of treating a mammal having a condition where inhibition of PDE4 provides a benefit, modulating cAMP levels in a mammal, reducing TNFα levels in a mammal of suppressing inflammatory cell activation in a mammal, and inhibiting PDE4 function in a mammal by administering therapeutically effective amounts of a compound of structural formula (II), or a composition containing a composition of structural formula (II) to the mammal.

DETAILED DESCRIPTION OF THE PREFERRED EMBODIMENTS

The present invention is directed to compounds having the structural formula (II):

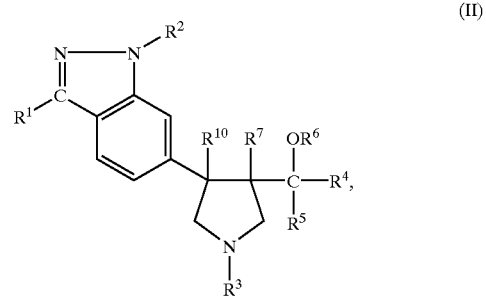

(II)

wherein $R^1$ is hydrogen, lower alkyl, bridged alkyl (e.g., norbornyl), aryl (e.g., phenyl), cycloalkyl, a 5- or 6-membered saturated heterocycle (e.g., 3-tetrahydrofuryl), $C_{1-3}$alkylenecycloalkyl (e.g., cyclopentylmethyl), aryl- or heteroaryl-substituted propargyl (i.e., —$CH_2C \equiv C$—$C_6H_5$), aryl- or heteroaryl-substituted allyl (e.g., —$CH_2CH = CH$—$C_6H_5$), or halocycloalkyl (e.g., fluorocyclopentyl);

$R^2$ is hydrogen, lower alkyl, bridged alkyl, cycloalkyl, haloalkyl, halocycloalkyl, $C_{1-3}$alkylenecycloalkyl, a 5- or 6-membered saturated heterocycle, aryl, heteroaryl, aralkyl, alkaryl, heteroaralkyl, or heteroalkaryl;

$R^3$ is $C(=O)OR^7$, $C(=O)R^7$, $C(=NH)NR^8R^9$, $C(=O)$-$NR^8R^9$, lower alkyl, bridged alkyl, cycloalkyl, haloalkyl, halocycloalkyl, $C_{1-3}$alkylenecycloalkyl, a 5- or 6-membered saturated heterocycle, aryl, heteroaryl, heteroaryl$SO_2$, aralkyl, alkaryl, heteroaralkyl, heteroalkaryl, $C_{1-3}$alkyleneC$(=O)OR^7$, $C(=O)C_{1-3}$alkylene-C$(=O)OR^7$, $C_{1-3}$alkyleneheteroaryl, $C(=O)C(=O)OR^7$, $C(=O)C_{1-3}$alkyleneC$(=O)OR^7$, $C(=O)C_{1-3}$alkyleneNH$(C=O)OR^7$, $C(=O)C_{1-3}$alkyleneNH$_2$, or NHC$(=O)OR^7$.

$R^4$ is hydrogen, lower alkyl, haloalkyl, cycloalkyl, or aryl;

$R^5$ is hydrogen, lower alkyl, alkynyl, haloalkyl, cycloalkyl, or aryl;

$R^6$ is hydrogen, lower alkyl, or $C(=O)R^7$;

$R^7$ is lower alkyl, branched or unbranched, or aryl, either optionally substituted with one or more of $OR^8$, $NR^8R^9$, or $SR^8$; and $R^8$ and $R^9$, same or different, are selected from the group consisting of hydrogen, lower alkyl, cycloalkyl, aryl, heteroaryl, alkaryl, heteroaralkyl, heteroalkaryl, and aralkyl, or $R^8$ and $R^9$ together form a 4-membered to 7-membered ring;

$R^{10}$ is hydrogen, alkyl, haloalkyl, cycloalkyl, aryl, $C(=O)$alkyl, $C(=O)$cycloalkyl, $C(=O)$aryl, $C(=O)$Oalkyl, $C(=O)$Ocycloalkyl, $C(=O)$aryl, $CH_2OH$, $CH_2O$alkyl, CHO, CN, $NO_2$, or $SO_2R^{11}$; and $R^{11}$ is alkyl, cycloalkyl, trifluoromethyl, aryl, aralkyl, or $NR^8R^9$.

As used herein, the term "alkyl," alone or in combination, is defined to include straight and branched chain, and bridged, saturated hydrocarbon groups containing one to 16 carbon atoms. The term "lower alkyl" is defined herein as an alkyl group having one through six carbon atoms ($C_1$–$C_6$). Examples of lower alkyl groups include, but are not limited to, methyl, ethyl, n-propyl, isopropyl, isobutyl, n-butyl, neopentyl, n-hexyl, and the like. The term "alkynyl" refers to an unsaturated alkyl group that contains a carbon-carbon triple bond.

The term "bridged alkyl" is defined herein as a $C_6$–$C_{16}$ bicyclic or polycyclic hydrocarbon group, for example, norboryl, adamantyl, bicyclo[2.2.2]-octyl, bicyclo[2.2.1] heptyl, bicyclo[3.2.1]octyl, or decahydronaphthyl.

The term "cycloalkyl" is defined herein to include cyclic $C_3$–$C_7$ hydrocarbon groups. Examples of cycloalkyl groups include, but are not limited to, cyclopropyl, cyclobutyl, cyclohexyl, and cyclopentyl.

The term "alkylene" refers to an alkyl group having a substituent. For example, the term "$C_{1-3}$alkylenecycloalkyl" refers to an alkyl group containing one to three carbon atoms, and substituted with a cycloalkyl group.

The term "haloalkyl" is defined herein as an alkyl group substituted with one or more halo substituents, either fluro, chloro, bromo, iodo, or combinations thereof. Similarly, "halocoalkyl" is defined as a cycloalkyl group having one more halo substituents.

The term "aryl," alone or in combination, is defined herein as a monocyclic or polycyclic aromatic group, preferably a monocyclic or bicyclic aromatic group, e.g., phenyl or naphthyl, that can be unsubstituted or substituted, for example, with one or more, and in particular one to three, substituents selected from halo, alkyl, hydroxy, hydroxyalkyl, alkoxy, alkoxyalkyl, haloalkyl, nitro, amino, alkylamino, acylamino, alkylthio, alkylsulfinyl, and alkylsulfonyl. Exemplary aryl groups include phenyl, naphthyl, tetrahydronaphthyl, 2-chlorophenyl, 3-chlorophenyl, 4-chlorophenyl, 2-methylphenyl, 4-methoxyphenyl, 3-trifluoromethylphenyl, 4-nitrophenyl, and the like.

The term "heteroaryl" is defined herein as a monocyclic or bicyclic ring system containing one or two aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, amino, alkylamino, acylamino, alkylthio, alkylsulfinyl, and alkylsulfonyl. Examples of heteroaryl groups include thienyl, furyl, pyridyl, oxazolyl, quinolyl, isoquinolyl, indolyl, triazolyl, isothiazolyl, isoxazolyl, imidizolyl, benzothiazolyl, pyrazinyl, pyrimidinyl, thiazolyl, and thiadiazolyl.

The term "aralkyl" is defined herein as a previously defined alkyl group, wherein one of the hydrogen atoms is replaced by an aryl group as defined herein, for example, a phenyl group optionally having one or more substituents, for example, halo, alkyl, alkoxy, and the like. An example of an aralkyl group is a benzyl group.

The term "alkaryl" is defined herein as a previously defined aryl group, wherein one of the hydrogen atoms is replaced by an alkyl, cycloalkyl, haloalkyl, or halocycloalkyl group.

The terms "heteroaralkyl" and "heteroalkaryl" are defined similarly as the term "aralkyl" and "alkaryl," however, the aryl group is replaced by a heteroaryl group as previously defined.

The term "heterocycle" is defined as a 5- or 6-membered nonaromatic ring having one or more heteroatoms selected from oxygen, nitrogen, and sulfur present in the ring.

Nonlimiting examples include tetrahydrofuran, piperidine, piperazine, sulfolane, morpholine, tetrahydropyran, dioxane, and the like.

The term "halogen" or "halo" is defined herein to include fluorine, chlorine, bromine, and iodine.

The terms "alkoxy," "aryloxy," and "aralkoxy" are defined as —OR, wherein R is alkyl, aryl, and aralkyl, respectively.

The term "alkoxyalkyl" is defined as an alkoxy group appended to an alkyl group. The terms "aryloxyalkyl" and "aralkoxyalkyl" are similarly defined as an aryloxy or aralkoxy group appended to an alkyl group.

The term "hydroxy" is defined as —OH.

The term "hydroxyalkyl" is defined as a hydroxy group appended to an alkyl group.

The term "amino" is defined as —NH.

The term "alkylamino" is defined as —NR$_2$, wherein at least one R is alkyl and the second R is alkyl or hydrogen.

The term "acylamino" is defined as RC(=O)N, wherein R is alkyl or aryl.

The term "nitro" is defined as —NO$_2$.

The term "alkylthio" is defined as —SR, where R is alkyl.

The term "alkylsulfinyl" is defined as R—SO$_2$, where R is alkyl.

The term "alkylsulfonyl" is defined as R—SO$_3$, where R is alkyl.

In preferred embodiments, $R^5$ is hydrogen or methyl; $R^7$ is methyl; $R^2$ is alkyl, cycloalkyl, aryl, or heteroaryl; $R^4$ is selected from the group consisting of hydrogen, methyl, trifluoromethyl, and cyclopropyl; $R^6$ is selected from the group consisting of hydrogen, acetyl, and benzoyl; $R^1$ is selected from the group consisting of hydrogen, alkyl, cycloalkyl, $C_{1-3}$alkylenecycloalkyl, halocycloalkyl, aryl, and heteroaryl; $R^4$ is selected from the group consisting of C(=O)OR$^7$, aralkyl, alkaryl, heteroaralkyl, heteroalkaryl, lower alkyl, cycloalkyl, a heterocycle, and aryl, and particularly

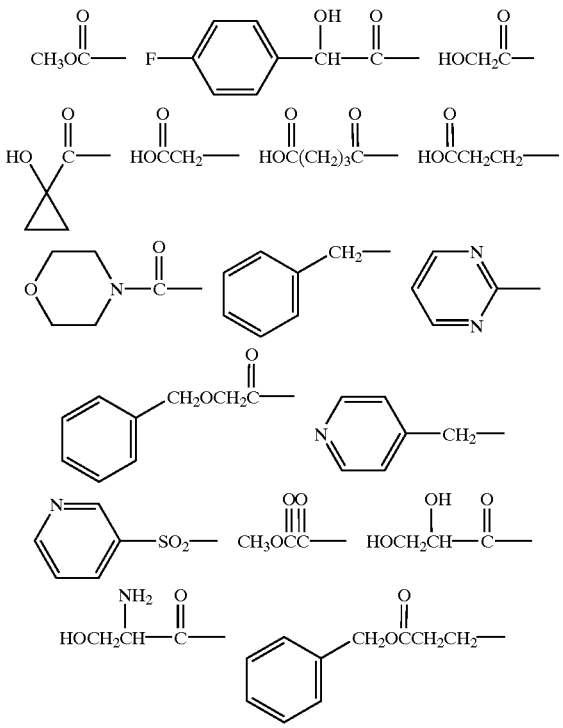

-continued

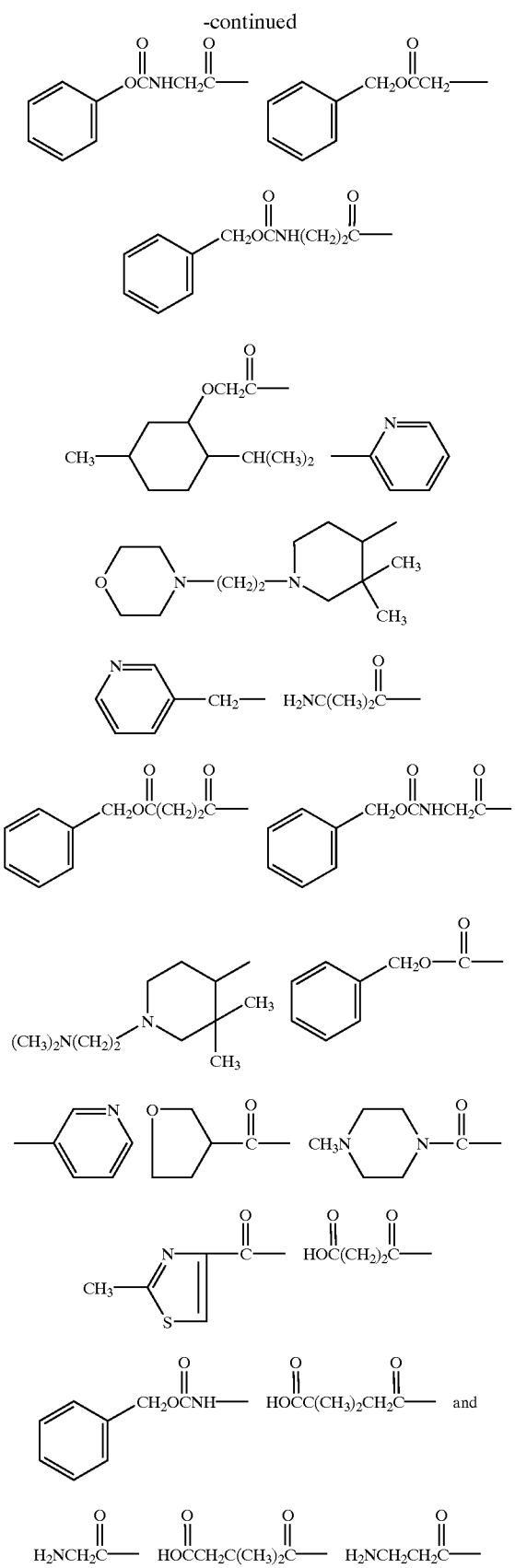

In most preferred embodiments, $R^1$ is selected from the group consisting of cyclopentyl, tetrahydrofuryl, indanyl, norbornyl, phenethyl, and phenylbutyl; $R^2$ is selected from the group consisting of hydrogen, ethyl, methyl, and difluoromethyl; $R^3$ is selected from the group consisting of benzyl, $CO_2CH_3$, $C(=O)CH_2OH$, $C(=O)CH(CH_3)OH$, $C(=O)C(CH_3)_2OH$, and

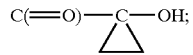

$R^4$ is hydrogen; $R^5$ is hydrogen or methyl; $R^6$ is hydrogen; $R^7$ is methyl; and $R^{10}$ is hydrogen.

The present invention includes all possible stereoisomers and geometric isomers of compounds of structural formula (II), and includes not only racemic compounds but also the optically active isomers as well. When a compound of structural formula (II) is desired as a single enantiomer, it can be obtained either by resolution of the final product or by stereospecific synthesis from either isomerically pure starting material or use of a chiral auxiliary reagent, for example, see Z. Ma et al., *Tetrahedron: Asymmetry*, 8(6), pages 883–888 (1997). Resolution of the final product, an intermediate, or a starting material can be achieved by any suitable method known in the art. Additionally, in situations where tautomers of the compounds of structural formula (II) are possible, the present invention is intended to include all tautomeric forms of the compounds. As demonstrated hereafter, specific stereoisomers exhibit an exceptional ability to inhibit PDE4 without manifesting the adverse CNS side effects typically associated with PDE4 inhibitors.

In particular, it s generally accepted that biological systems can exhibit very sensitive activities with respect to the absolute stereochemical nature of compounds. (See, E. J. Ariens, *Medicinal Research Reviews*, 6:451–466 (1986); E. J. Ariens, *Medicinal Research Reviews*, 7:367–387 (1987); K. W. Fowler, Handbook of Stereoisomers: Therapeutic Drugs, CRC Press, edited by Donald P. Smith, pp. 35–63 (1989); and S. C. Stinson, *Chemical and Engineering News*, 75:38–70 (1997).)

For example, rolipram is a stereospecific PDE4 inhibitor that contains one chiral center. The (−)-enantiomer of rolipram has a higher pharmacological potency than the (+)-enantiomer, which could be related to its potential antidepressant action. Schultz et al., *Naunyn-Schmiedeberg's Arch Pharmacol*, 333:23–30 (1986). Furthermore, the metabolism of rolipram appears stereospecific with the (+)-enantiomer exhibiting a faster clearance rate than the (−)-enantiomer. Krause et al., *Xenobiotica*, 18:561–571 (1988). Finally, a recent observation indicated that the (−)-enantiomer of rolipram (R-rolipram) is about ten-fold more emetic than the (+)-enantiomer (S-rolipram). A. Robichaud et al., *Neuropharmacology*, 38:289–297 (1999). This observation is not easily reconciled with differences in test animal disposition to rolipram isomers and the ability of rolipram to inhibit the PDE4 enzyme. The compounds of the present invention can have three chiral centers. Compounds of a specific stereochemical orientation can exhibit similar PDE4 inhibitory activity and pharmacological activity, but altered CNS toxicity and emetic potential.

Accordingly, preferred compounds of the present invention have the structural formula (III):

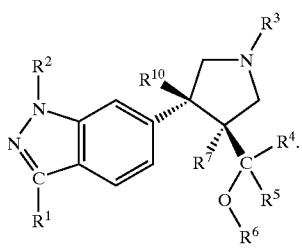

(III)

The compounds of structural formula (III) are potent and selective PDE4 inhibitors, and do not manifest the adverse CNS effects and emetic potential demonstrated by stereoisomers of a compound of structural formula (III).

Compounds of structural formula (II) which contain acidic moieties can form pharmaceutically acceptable salts with suitable cations. Suitable pharmaceutically acceptable cations include alkali metal (e.g., sodium or potassium) and alkaline earth metal (e.g., calcium or magnesium) cations. The pharmaceutically acceptable salts of the compounds of structural formula (II), which contain a basic center, are acid addition salts formed with pharmaceutically acceptable acids. Examples include the hydrochloride, hydrobromide, sulfate or bisulfate, phosphate or hydrogen phosphate, acetate, benzoate, succinate, fumarate, maleate, lactate, citrate, tartraze, gluconate, methanesulfonate, benzenesulphonate, and p-toluenesulphonate salts. In light of the foregoing, any reference to compounds of the present invention appearing herein is intended to include compounds of structural formula (II), as well as pharmaceutically acceptable salts and solvates thereof.

The compounds of the present invention can be therapeutically administered as the neat chemical, but it is preferable to administer compounds of structural formula (II) as a pharmaceutical composition or formulation. Accordingly, the present invention further provides for pharmaceutical formulations comprising a compound of structural formula (II), or pharmaceutically acceptable salts thereof, together with one or more pharmaceutically acceptable carriers and, optionally, other therapeutic and/or prophylactic ingredients. The carriers are "acceptable" in the sense of being compatible with the other ingredients of the formulation and not deleterious to the recipient thereof.

In particular, a selective PDE4 inhibitor of the present invention is useful alone or in combination with a second antiinflammatory therapeutic agent, for example, a therapeutic agent targeting TNFα, such as ENBREL® or REMICADE®, which have utility in treating rheumatoid arthritis. Likewise, therapeutic utility of IL-1 antagonism has also been shown in animal models for rheumatoid arthritis. Thus, it is envisioned that IL-1 antagonism, in combination with PDE4 inhibition, which attenuates TNFα, would be efficacious.

The present PDE4 inhibitors are useful in the treatment of a variety of allergic, autoimmune, and inflammatory diseases.

The term "treatment" includes preventing, lowering, stopping, or reversing the progression of severity of the condition or symptoms being treated. As such, the term "treatment" includes both medical therapeutic and/or prophylactic administration, as appropriate.

In particular, inflammation is a localized, protective response elicited by injury or destruction of tissues, which serves to destroy, dilute or wall off (i.e., sequester) both the injurious agent and the injured tissue. The term "inflammatory disease," as used herein, means any disease in which an excessive or unregulated inflammatory response leads to excessive inflammatory symptoms, host tissue damage, or loss of tissue function. Additionally, the term "autoimmune disease," as used herein, means any group of disorders in which tissue injury is associated with humoral or cell-mediated responses to the body's own constituents. The term "allergic disease," as used herein, means any symptoms, tissue damage, or loss of tissue function resulting from allergy. The term "arthritic disease," as used herein, means any of a large family of diseases that are characterized by inflammatory lesions of the joints attributable to a variety of etiologies. The term "dermatitis," as used herein, means any of a large family of diseases of the skin that are characterized by inflammation of the skin attributable to a variety of etiologies. The term "transplant rejection," as used herein, means any immune reaction directed against grafted tissue (including organ and cell (e.g., bone marrow)), characterized by a loss of function of the grafted and surrounding tissues, pain, swelling, leukocytosis and thrombocytopenia.

The present invention also provides a method of modulating cAMP levels in a mammal, as well as a method of treating diseases characterized by elevated cytokine levels. The term "cytokine," as used herein, means any secreted polypeptide that affects the functions of other cells, and that modulates interactions between cells in the immune or inflammatory response. Cytokines include, but are not limited to monokines, lymphokines, and chemokines regardless of which cells produce them. For instance, a monokine is generally referred to as being produced and secreted by a monocyte, however, many other cells produce monokines, such as natural killer cells, fibroblasts, basophils, neutrophils, endothelial cells, brain astrocytes, bone marrow stromal cells, epidermal keratinocytes, and B-lymphocytes. Lymphokines are generally referred to as being produced by lymphocyte cells. Examples of cytokines include, but are not limited to, interleukin-1 (IL-1), interleukin-6 (IL-6), Tumor Necrosis Factor alpha (TNFα), and Tumor Necrosis Factor beta (TNFβ).

The present invention further provides a method of reducing TNF levels in a mammal, which comprises administering an effective amount of a compound of structural formula (II) to the mammal. The term "reducing TNF levels," as used herein, means either:

a) decreasing excessive in vivo TNF levels in a mammal to normal levels or below normal levels by inhibition of the in vivo release of TNF by all cells, including but not limited to monocytes or macrophages; or b) inducing a down-regulation, at the translational or transcription level, of excessive in vivo TNF levels in a mammal to normal levels or below normal levels; or c) inducing a down-regulation, by inhibition of the direct synthesis of TNF as a postranslational event.

Moreover, the compounds of the present invention are useful in suppressing inflammatory cell activation. The term "inflammatory cell activation," as used herein, means the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatability antigens or cell adhesion molecules) in inflammatory cells (including but not limited to monocytes, macrophages, T lymphocytes, B lymphocytes, granulocytes, polymorphonuclear leukocytes, mast cells, basophils, eosinophils, dendritic cells, and endothelial cells). It will be appreciated by persons skilled in the art that the activation of one or a combination of these phenotypes in these cells can contribute to the initiation, perpetuation, or exacerbation of an inflammatory condition.

The compounds of the present invention also are useful in causing airway smooth muscle relaxation, bronchodilation, and prevention of bronchoconstriction.

The compounds of the present invention, therefore, are useful in treating such diseases as arthritic diseases (such as rheumatoid arthritis), osteoarthritis, gouty arthritis, spondylitis, thyroid-associated ophthalmopathy, Behcet disease, sepsis, septic shock, endotoxic shock, gram negative sepsis, gram positive sepsis, toxic shock syndrome, asthma, chronic bronchitis, allergic rhinitis, allergic conjunctivitis, vernal conjunctivitis, eosinophilic granuloma, adult (acute) respiratory distress syndrome (ARDS), chronic pulmonary inflammatory disease (such as chronic obstructive pulmonary disease), silicosis, pulmonary sarcoidosis, reperfusion injury of the myocardium, brain or extremities, brain or spinal cord injury due to minor trauma, fibrosis including cystic fibrosis, keloid formation, scar tissue formation, atherosclerosis, autoimmune diseases, such as systemic lupus erythematosus (SLE) and transplant rejection disorders (e.g., graft vs. host (GvH) reaction and allograft rejection), chronic glomerulonephritis, inflammatory bowel diseases, such as Crohn's disease and ulcerative colitis, proliferative lymphocytic diseases, such as leukemias (e.g. chronic lymphocytic leukemia; CLL) (see Mentz et al., *Blood* 88, pp. 2172–2182 (1996)), and inflammatory dermatoses, such as atopic dermatitis, psoriasis, or urticaria.

Other examples of such diseases or related conditions include cardiomyopathies, such as congestive heart failure, pyrexia, cachexia, cachexia secondary to infection or malignancy, cachexia secondary to acquired immune deficiency syndrome (AIDS), ARC (AIDS-related complex), cerebral malaria, osteoporosis and bone resorption diseases, and fever and myalgias due to infection. In addition, the compounds of the present invention are useful in the treatment of diabetes insipidus and central nervous system disorders, such as depression and multi-infarct dementia.

Compounds of the present invention also have utility outside of that typically known as therapeutic. For example, the present compounds can function as organ transplant preservatives (see Pinsky et al., *J. Clin. Invest.*, 92, pp. 2994–3002 (1993)) as well.

Selective PDE4 inhibitors also can be useful in the treatment of diabetes insipidus (*Kidney Int.*, 37, p. 362, (1990); *Kidney Int.*, 35, p. 494, (1989)) and central nervous system disorders, such as multiinfarct dementia (Nicholson, *Psychopharmacology*, 101, p. 147 (1990)), depression (Eckman et al., *Curr. Ther. Res.*, 43, p. 291 (1988)), anxiety and stress responses (*Neuropharmacology*, 38, p. 1831 (1991)), cerebral ischemia (*Eur. J. Pharmacol.*, 272, p. 107 (1995)), tardive dyskinesia (*J. Clin. Pharmocol.*, 16, p. 304 (1976)), Parkinson's disease (see *Neurology*, 25, p. 722 (1975); *Clin. Exp. Pharmacol, Physiol.*, 26, p. 421 (1999)), and premenstrual syndrome. With respect to depression, PDE4-selective inhibitors show efficacy in a variety of animal models of depression such as the "behavioral despair" or Porsolt tests (*Eur. J. Pharmacol.*, 47, p. 379 (1978); *Eur. J. Pharmacol.*, 57, p. 431 (1979); *Antidepressants: neurochemical, behavioral and clinical prospectives*, Enna, Malick, and Richelson, eds., Raven Press, p. 121 (1981)), and the "tail suspension test" (*Psychopharmacology*, 85, p. 367 (1985)). Recent research findings show that chronic in vivo treatment by a variety of antidepressants increase the brain-derived expression of PDE4 (*J. Neuroscience*, 19, p. 610 (1999)). Therefore, a selective PDE4 inhibitor can be used alone or in conjunction with a second therapeutic agent in a treatment for the four major classes of antidepressants: electroconvulsive procedures, monoamine oxidase inhibitors, and selective reuptake inhibitors of serotonin or norepinephrine. Selective PDE4 inhibitors also can be useful in applications that modulate bronchodilatory activity via direct action on bronchial smooth muscle cells for the treatment of asthma.

Compounds and pharmaceutical compositions suitable for use in the present invention include those wherein the active ingredient is administered to a mammal in an effective amount to achieve its intended purpose. More specifically, a "therapeutically effective amount" means an amount effective to prevent development of, or to alleviate the existing symptoms of, the subject being treated. Determination of the effective amounts is well within the capability of those skilled in the art, especially in light of the detailed disclosure provided herein.

The term "mammal" as used herein includes males and females, and encompasses humans, domestic animals (e.g., cats, dogs), livestock (e.g., cattle, horses, swine), and wildlife (e.g., primates, large cats, zoo specimens).

A "therapeutically effective dose" refers to that amount of the compound that results in achieving the desired effect. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. Compounds which exhibit high therapeutic indices are preferred. The data obtained from such data can be used in formulating a dosage range for use in humans. The dosage of such compounds preferably lies within a range of circulating concentrations that include the $ED_{50}$ with little or no toxicity. The dosage can vary within this range depending upon the dosage form employed, and the route of administration utilized.

The exact formulation, route of administration, and dosage can be chosen by the individual physician in view of the patient's condition. Dosage amount and interval can be adjusted individually to provide plasma levels of the active moiety which are sufficient to maintain the therapeutic effects.

As appreciated by persons skilled in the art, reference herein to treatment extends to prophylaxis, as well as to treatment of established diseases or symptoms. It is further appreciated that the amount of a compound of the invention required for use in treatment varies with the nature of the condition being treated, and with the age and the condition of the patient, and is ultimately determined by the attendant physician or veterinarian. In general, however, doses employed for adult human treatment typically are in the range of 0.001 mg/kg to about 100 mg/kg per day. The desired dose can be conveniently administered in a single dose, or as multiple doses administered at appropriate intervals, for example as two, three, four or more subdoses per day. In practice, the physician determines the actual dosing regimen which is most suitable for an individual patient, and the dosage varies with the age, weight, and response of the particular patient. The above dosages are exemplary of the average case, but there can be individual instances in which higher or lower dosages are merited, and such are within the scope of the present invention.

Formulations of the present invention can be administered in a standard manner for the treatment of the indicated diseases, such as orally, parenterally, transmucosally (e.g., sublingually or via buccal administration), topically, transdermally, rectally, via inhalation (e.g., nasal or deep lung inhalation). Parenteral administration includes, but is not limited to intravenous, intraarterial, intraperitoneal, subcutaneous, intramuscular, intrathecal, and intraarticular. Parenteral administration also can be accomplished using a high pressure technique, like POWDERJECT™.

For buccal administration, the composition can be in the form of tablets or lozenges formulated in conventional manner. For example, tablets and capsules for oral administration can contain conventional excipients such as binding agents (for example, syrup, accacia, gelatin, sorbitol, tragacanth, mucilage of starch or polyvinylpyrrolidone), fillers (for example, lactose, sugar, microcrystalline, cellulose, maize-starch, calcium phosphate or sorbitol), lubricants (for example, magnesium, stearate, stearic acid, talc, polyethylene glycol or silica), disintegrants (for example, potato starch or sodium starch glycollate), or wetting agents (for example, sodium lauryl sulfate). The tablets can be coated according to methods well known in the art.

Alternatively, the compounds of the present invention can be incorporated into oral liquid preparations such as aqueous or oily suspensions, solutions, emulsions, syrups, or elixirs, for example. Moreover, formulations containing these compounds can be presented as a dry product for constitution with water or other suitable vehicle before use. Such liquid preparations can contain conventional additives, such as suspending agents, such as sorbitol syrup, methyl cellulose, glucose/sugar syrup, gelatin, hydroxyethylcellulose, hydroxypropylmethylcellulose, carboxymethyl cellulose, aluminum stearate gel, and hydrogenated edible fats; emulsifying agents, such as lecithin, sorbitan monooleate, or acacia; nonaqueous vehicles (which can include edible oils), such as almond oil, fractionated coconut oil, oily esters, propylene glycol, and ethyl alcohol; and preservatives, such as methyl or propyl p-hydroxybenzoate and sorbic acid.

Such preparations also can be formulated as suppositories, e.g., containing conventional suppository bases, such as cocoa butter or other glycerides. Compositions for inhalation typically can be provided in the form of a solution, suspension, or emulsion that can be administered as a dry powder or in the form of an aerosol using a conventional propellant, such as dichlorodifluoromethane or trichlorofluoromethane. Typical topical and transdermal formulations comprise conventional aqueous or nonaqueous vehicles, such as eye drops, creams, ointments, lotions, and pastes, or are in the form of a medicated plaster, patch, or membrane.

Additionally, compositions of the present invention can be formulated for parenteral administration by injection or continuous infusion. Formulations for injection can be in the form of suspensions, solutions, or emulsions in oily or aqueous vehicles, and can contain formulation agents, such as suspending, stabilizing, and/or dispersing agents. Alternatively, the active ingredient can be in powder form for constitution with a suitable vehicle (e.g., sterile, pyrogen-free water) before use.

A composition in accordance with the present invention also can be formulated as a depot preparation. Such long acting formulations can be administered by implantation (for example, subcutaneously or intramuscularly) or by intramuscular injection. Accordingly, the compounds of the invention can be formulated with suitable polymeric or hydrophobic materials (e.g., an emulsion in an acceptable oil), ion exchange resins, or as sparingly soluble derivatives (e.g., a sparingly soluble salt).

For veterinary use, a compound of formula (II), or nontoxic salts thereof, is administered as a suitably acceptable formulation in accordance with normal veterinary practice. The veterinarian can readily determine the dosing regimen and route of administration that is most appropriate for a particular animal.

Thus, the invention provides in a further aspect a pharmaceutical composition comprising a compound of the formula (II), together with a pharmaceutically acceptable diluent or carrier therefor. There is further provided by the present invention a process of preparing a pharmaceutical composition comprising a compound of formula (II), which process comprises mixing a compound of formula (II), together with a pharmaceutically acceptable diluent or carrier therefor.

Specific, nonlimiting examples of compounds of structural formula (II) are provided below, the synthesis of which were performed in accordance with the procedures set forth below.

Generally, compounds of structural formula (II) can be prepared according to the following synthetic scheme. In the scheme described below, it is understood in the art that protecting groups can be employed where necessary in accordance with general principles of synthetic chemistry. These protecting groups are removed in the final steps of the synthesis under basic, acidic, or hydrogenolytic conditions which are readily apparent to those skilled in the art. By employing appropriate manipulation and protection of any chemical functionalities, synthesis of compounds of structural formula (II) not specifically set forth herein can be accomplished by methods analogous to the schemes set forth below.

Unless otherwise noted, all starting materials were obtained from commercial suppliers and used without further purification. All reactions and chromatography fractions were analyzed by thin-layer chromatography on 250-mm silica gel plates, visualized with UV (ultraviolet) light or $I_2$ (iodine) stain. Products and intermediates were purified by flash chromatography, or reverse-phase HPLC.

The compounds of general structural formula (II) can be prepared, for example, as set forth in the following synthetic scheme. Other synthetic routes also are known to persons skilled in the art. The following reaction scheme provides a compound of structural formula (II), wherein $R^1$ and $R^2$, i.e., $C_2H_5$ and cyclopentyl, are determined by the starting materials. Proper selection of other starting materials, or performing conversion reactions on intermediates and examples, provide compounds of general structural formula (II) having other recited $R^1$ through $R^{11}$ substituents.

The following illustrates the synthesis of various intermediates and compounds of structural formula (II). The following examples are provided for illustration and should not be construed as limiting.

General Synthesis of Indazole Compounds
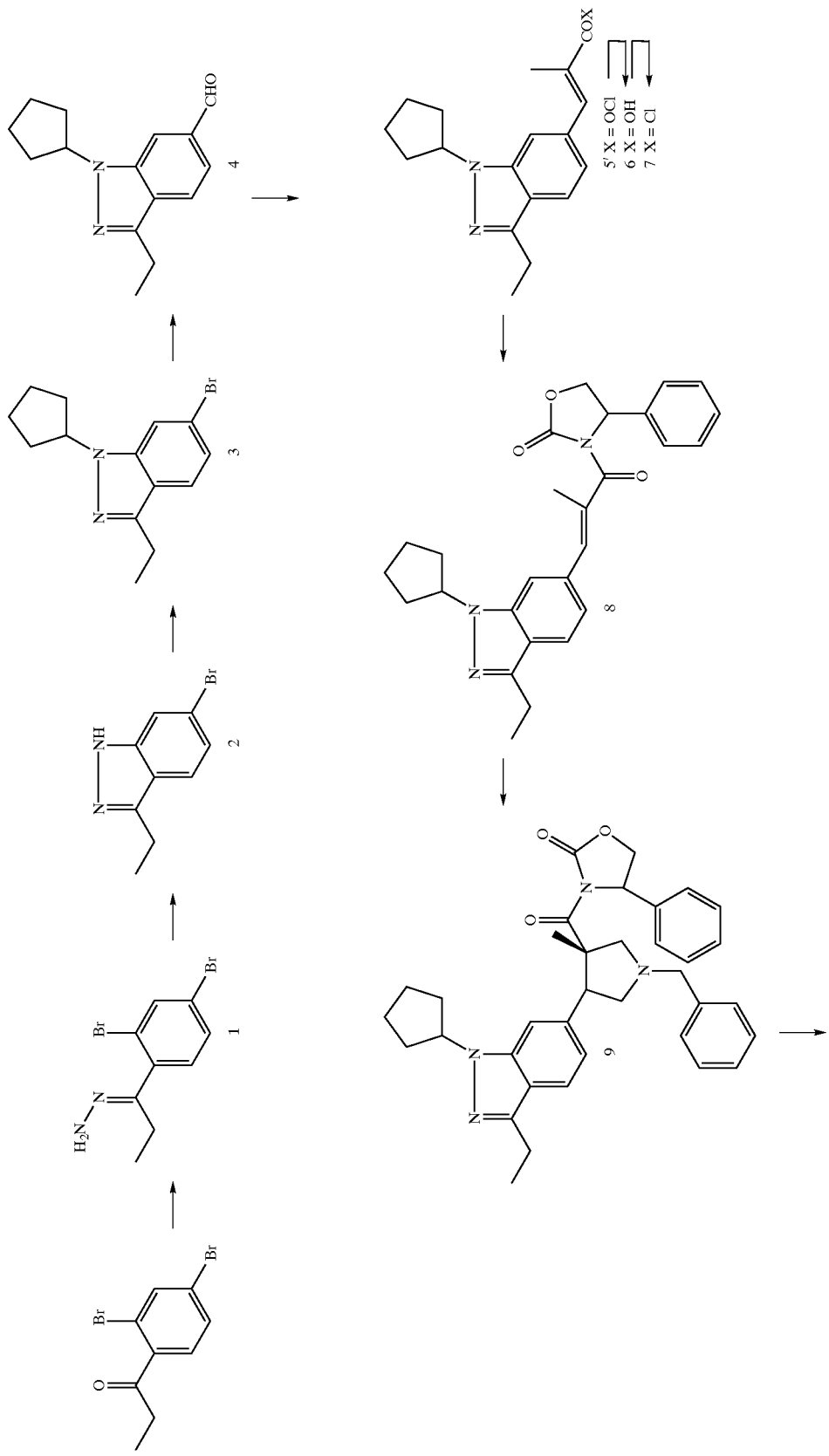

-continued
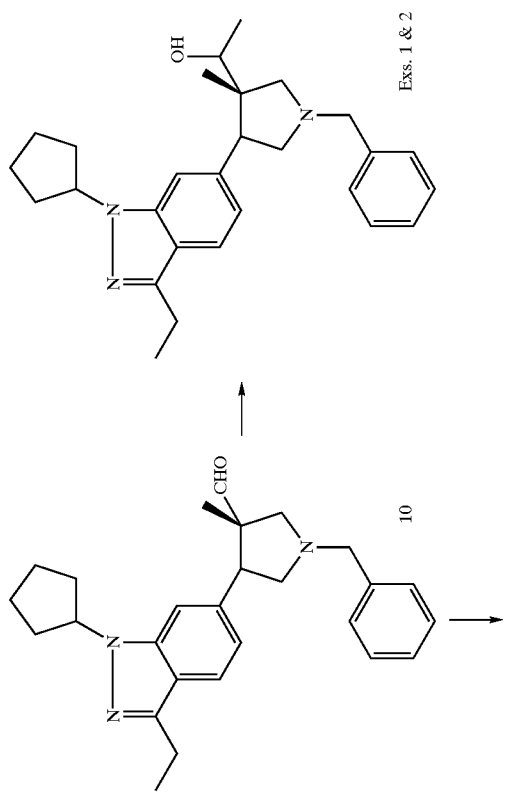
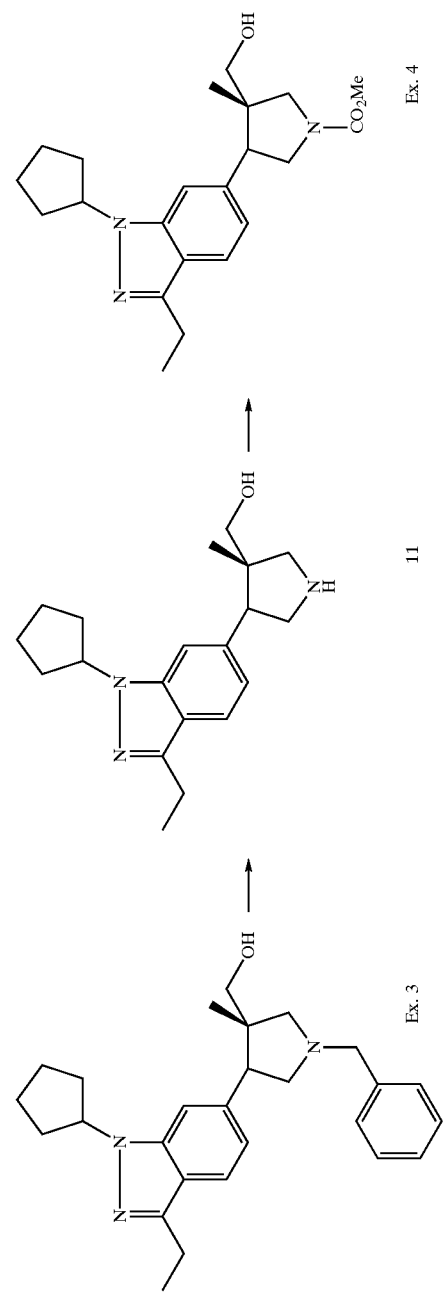

INTERMEDIATE 1

Preparation of 1-(2,4-Dibromophenyl)propan-1-hydrazone

Hydrazine (18.4 mL; 589 mmol) was added to a stirred solution of 1-(2,4-dibromophenyl)propan-1-one (17.2 g; 58.9 mmol), available from Aldrich Chemical Co., Milwaukee, Wis., in dry ethanol (400 mL) at room temperature under nitrogen atmosphere. The resulting solution was heated at 80° C. overnight. The reaction was allowed to cool to room temperature, then was concentrated at reduced pressure. The resulting oil was dissolved in dichloromethane (400 mL), dried over sodium sulfate ($Na_2SO_4$), filtered, then concentrated in vacuo to provide the named hydrazone (16.5 g; 92%). This compound was used without further purification or characterization.

INTERMEDIATE 2

Preparation of 6-Bromo-3-ethyl-1H-indazole

Sodium Hydride Procedure:

A stirred solution of Intermediate 1 (16.5 g; 54 mmol) in dry dimethylformamide (350 mL) was added sodium hydride (60% dispersion in oil; 5.72 g; 108 mmol) at room temperature under a nitrogen atmosphere. The resulting mixture was heated at 79° C. for 2.5 hours, then allowed to cool to room temperature. About one-half of the solvent was removed by concentration at reduced pressure, then the reaction mixture was diluted with water (800 mL). After stirring for 1 hour, the resulting mixture was extracted with ethyl acetate (3×300 mL) and the combined organic layers were washed with brine (2×200 mL), dried over $Na_2SO_4$, filtered, and concentrated in vacuo. The residual oil was passed through a plug of silica gel with hexanes/ethyl acetate eluent (1:1) to provide the named indazole (12.26 g; 99%).

$^1$H NMR ($CDCl_3$, 400 MHz): δ 9.98 (br s, 1H), 7.60 (d, 1H), 7.57 (d, 1H), 7.24 (dd, 1H), 2.99 (q, 2H), 1.40 (t, 3H).

INTERMEDIATE 3

Preparation of 6-Bromo-1-cyclopentyl-3-ethyl-1H-indazole

To a stirred solution of Intermediate 2 (130 mg; 0.58 mmol) in dry dimethylformamide (5.8 mL) was added sodium hydride (60% oil dispersion; 26 mg; 0.64 mmol) at 0° C. under a nitrogen atmosphere. The reaction mixture was allowed to warm to room temperature for 30 minutes, then was treated with cyclopentyl bromide (68 μL; 0.63 mmol). After stirring overnight, the reaction mixture was partitioned between ethyl acetate (50 mL) and water (50 mL), then the organics were isolated and washed (4×50 mL) with water. The reaction was dried over $MgSO_4$, filtered, and concentrated in vacuo. TLC in 5/95 ethyl acetate/hexanes indicated a 5:1 mixture of regioisomers were formed with the desired, higher $R_f$, N-1 alkylated product being major. Flash chromatography in 5/95 ethyl acetate/hexanes gave Intermediate 3 as a yellow oil (133 mg; 78%).

$^1$H NMR ($CDCl_3$, 400 MHz) δ 7.56 (d, 1H), 7.52 (d, 1H), 7.17 (dd, 1H), 4.83 (c, 1H), 2.95 (q, 2H), 2.28–2.07 (m, 4H), 2.00–1.93 (m, 2H), 1.76–1.66 (m, 2H), 1.36 (t, 3H).

INTERMEDIATE 4

Preparation of 1-Cyclopentyl-3-ethyl-1H-indazole-6-carbaldehyde

To a stirred, cooled (−78° C.) solution of Intermediate 3 (4.34 g; 14.9 mmol) in dry tetrahydrofuran (80 mL) was added n-butyllithium (7.51 mL of 1.98 M solution in hexanes; 14.9 mmol) via syringe under a nitrogen atmosphere. The resulting dark solution was stirred at −78° C. for 0.5 hour, then dimethylformamide (4.61 mL; 59.6 mmol) was added via syringe. After warming to 0° C. over 1 hour, the reaction mixture was quenched by the addition of water. Dilution with brine and extraction with ethyl acetate (3×100 mL), drying over $Na_2SO_4$, filtration, and concentration of the combined organic layers, provided crude Intermediate 4. Purification via flash chromatography (5% ethyl acetate in hexanes on silica gel) yielded the named aldehyde (2.55 g; 71%).

$^1$H NMR ($CDCl_3$, 400 MHz) δ 10.13 (s, 1H), 7.93 (s, 1H), 7.78 (d, 1H), 7.61 (d, 1H), 5.01 (c, 1H), 3.01 (q, 2H), 2.21–2.13 (m, 4H), 2.01–1.93 (m, 2H), 1.81–1.70 (m, 2H), 1.39 (t, 3H).

INTERMEDIATE 5

Preparation of Ethyl (2E)-3-(1-cyclopentyl-3-ethyl(1H-indazol-6-yl))-2-methylprop-2-enoate Prepared Via the Horner Emmons Olefination Procedure.

To a cooled (0° C.), stirred solution of triethylphosphonopropionate (364 μL, 1.70 mmol; 1.2 eq.) in dry tetrahydrofuran (14 mL) was added a solution of lithium hexamethyldisilylamide in tetrahydrofuran (1.56 mL of 1.0 M; 1.1 eq.) via syringe under a nitrogen atmosphere. The resulting yellow solution was stirred at 0° C. for 0.5 hours then a solution of Intermediate 4 (344 mg, 1.42 mmol) in dry tetrahydrofuran (1.0 mL) was added dropwise via addition funnel, over 5 minutes. The resulting solution was stirred at 0° C. for 2 hours, then warmed to room temperature and stirred overnight. The reaction then was quenched by the addition of water (30 mL) and extracted with ethyl acetate (2×20 mL). The combined organic layers were dried over magnesium sulfate ($MgSO_4$), filtered, and concentrated in vacuo. The crude product was purified by silica flash chromatography (6:1 hexanes: ethyl acetate) to yield the named ester as a clear, colorless liquid (418.6 mg, 90%).

$^1$H NMR ($CDCl_3$, 400 MHz): δ 7.83 (s, 1H), 7.67 (d, 1H), 7.40 (s, 1H), 7.13 (d, 1H), 4.91 (c, 1H), 4.29 (q, 2H), 2.99 (q, 2H), 2.18 (s, 3H), 2.17–2.10 (m, 4H), 1.99–1.92 (m, 2H), 1.78–1.70 (m, 2H), 1.42–1.33 (m, 6H).

INTERMEDIATE 6

Preparation of (2E)-3-(1-Cyclopentyl-3-ethyl(1H-indazol-6-yl))-2-methylprop-2-enoic Acid Prepared Via the Lithium Hydroxide Hydrolysis Procedure.

To a stirred solution of Intermediate 5 (1.05 g; 3.22 mmol) in THF (10 mL) was added a solution of lithium hydroxide monohydrate (676 mg; 16.1 mmol; 5.0 eq.) in water (10 mL) at room temperature under a nitrogen atmosphere. A slight exotherm occurred. The resulting cloudy yellow solution was heated at 65° C. (oil bath) overnight. After heating for 0.5 hour, the reaction became clear but required 1.5 hours for completion, as evaluated by TLC. The resulting solution was allowed to cool to room temperature, diluted with dichloromethane (30 mL), and washed with 1.0 M aqueous hydrochloric acid. The combined layers were washed with brine (30 mL), dried over $NaSO_4$, filtered, and concentrated in vacuo to provide the named carboxylic acid as a solid (890 mg; 93%).

1H NMR ($CDCl_3$, 400 MHz): δ 8.20 (s, 1H), 7.72 (d, 1H), 7.48 (s, 1H), 7.18 (dd, 1H), 4.94 (p, 1H), 3.00 (q, 2H), 2.26 (s, 3H), 2.25–2.13 (m, 4H), 2.03–1.93 (m, 2H), 1.80–1.72 (m, 2H), 1.40 (t, 3H).

INTERMEDIATE 7

Preparation of (2E)-3-(1-Cyclopentyl-3-ethyl(1H-indazol-6-yl))-2-methylprop-2-enoyl Chloride
Prepared Via the Acid Chloride Procedure.

To a cooled (0° C.), stirred slurry of Intermediate 6 (240 mg; 0.804 mmol) in anhydrous dichloromethane (6 mL) was added a solution of oxalyl chloride in dichloromethane (0.482 mL of 2.0 M; 0.964 mmol; 1.2 eq.) via syringe under a calcium chloride-dried atmosphere over a 10-minute period. Vigorous bubbling occurred. The resulting dark solution was allowed to stir at 0° C. for 15 minutes, then a catalytic amount of dimethylformamide was added via syringe (17 μL). The resulting solution was stirred at 0° C. for 0.5 hour until the bubbling subsided, then was allowed to warm to room temperature and stirred overnight (17 hours). The reaction was diluted with dichloromethane (15 mL), and was carefully quenched with water (20 mL). After vigorously stirring the resulting mixture for 1 hour, the layers were separated and the organic layer was washed with water (20 mL) and brine (20 mL), dried over $MgSO_4$, filtered, and concentrated in vacuo to provide the acid chloride as a brown solid (258 mg; 100%).

$^1$H NMR ($CDCl_3$, 400 MHz): δ 8.22 (s, 1H), 7.80 (d, 1H), 7.55 (s, 1H), 7.22 (dd, 1H), 4.99 (p, 1H), 3.00 (q, 2H), 2.29 (s, 3H), 2.26–2.19 (m, 4H), 2.06–1.94 (m, 2H), 1.82–1.75 (m, 2H), 1.41 (t, 3H).

INTERMEDIATE 8

Preparation of 3-[(2E)-3-(1-Cyclopentyl-3-ethyl(1H-indazol-6-yl))-2-methylprop-2-enoyl](4R)-4-phenyl-1,3-oxazolidin-2-one
Prepared Via the Oxazolidinone Acylation Procedure.

A solution of n-butyllithium in hexanes (0.429 mL of 1.98 M; 1.1 eq.) was added to a cooled (−78° C.), stirred solution of R-phenyl oxazolidinone (138.5 mg; 0.850 mmol) in dry tetrahydrofuran (7.7 mL) via syringe under a nitrogen atmosphere. The resulting solution was stirred at −78° C. for 0.8 hour, then a solution of the Intermediate 7 (269 mg; 0.8 mmol; 1.1 eq.) in tetrahydrofuran (1.5 mL) was added to the solution via cannulae. After stirring at −78° C. for 15 minutes, the resulting reaction mixture was allowed to slowly warm to 0° C. over 40 minutes during which time the reaction became a thick slurry. After stirring at 0° C. for 2.5 hours, the reaction mixture was diluted with ethyl acetate (30 mL) and washed with brine (2×30 mL). The organic layer was dried over $Na_2SO_4$ and concentrated in vacuo to provide Intermediate 8 as a white solid (426 mg; 100%).

$^1$H NMR ($CDCl_3$, 400 MHz): δ 7.65 (d, 1H), 7.43–7.30 (m, 7H), 7.11 (d, 1H), 5.56 (dd, 1H), 4.90 (p, 1H), 4.77 (t, 1H), 4.31 (dd, 1H), 2.98 (q, 2H), 2.20 (d, 3H), 2.18–2.13 (m, 4H), 1.98–1.91 (m, 2H), 1.76–1.69 (m, 2H), 1.38 (t, 3H).

INTERMEDIATE 9

Preparation of (4R)-3-{[(3S,4S)-4-(1-Cyclopentyl-3-ethyl(1H-indazol-6-yl))-3-methyl-1-benzylpyrrolidin-3-yl]carbonyl}-4-phenyl-1,3-oxazolidin-2-one
Prepared Via the Cycloaddition Procedure.

A solution of trifluoroacetic acid in chloroform (0.16 mL of 1.0 M; 0.17 mmol; 0.2 eq.) was added to a cooled (−4° C.), stirred slurry of Intermediate 8 (375 mg; 0.85 mmol) and N-(methoxy-methyl)-N-(trimethylsilylmethyl)benzylamine (334 mg; 1.70 mmol; 2 eq.) in chloroform (2.5 mL) via syringe under a nitrogen atmosphere. The resulting slurry was allowed to stir at about 0° C. for 4 hours, then at about 15° C. (water bath) overnight. The resulting cloudy solution then was cooled to −4° C., treated with additional N-(methoxymethyl)-N-trimethylsilyl-methyl)benzylamine (330 mg; 1.70 mmol; 2 eq.) via syringe, and stirred for 5 hours during which time the reaction mixture became homogenous. Thin layer chromatography (4:1 hexanes:EtOAc) showed that the reaction was completed. The bulk of the chloroform was removed under reduced pressure, and the residue was diluted with dichloromethane (30 mL). The resulting mixture was washed with brine (20 mL). The organic layer then was dried over $Na_2SO_4$, filtered, and concentrated in vacuo to give a semisolid. Purification of the semisolid via flash chromatography on silica gel (4:1 hexanes:EtoAc) provided the major diastereomer as a colorless foam (275 mg; 56%).

Major Diastereomer:

$^1$H NMR ($CDCl_3$, 400 MHz): δ 7.53 (d, 1H), 7.45–7.24 (m, 11H), 7.17 (d, 1H), 5.55 (dd, 1H), 4.87 (p, 1H), 4.70 (t, 1H), 4.31 (t, 1H), 4.22 (dd, 1H), 3.78 (d, 1H), 3.65 (d, 1H), 3.53 (d, 1H), 2.98–2.86 (m, 5H), 2.20–2.09 (m, 4H), 2.02–1.92 (m, 2H), 1.78–1.68 (m, 2H), 1.35 (t, 3H), 1.11 (s, 3H).

INTERMEDIATE 10

Preparation of (3S,4S)-4-(1-Cyclopentyl-3-ethyl (1H-indazol-6-yl))-3-methyl-1-benzylpyrrolidine-3-carbaldehyde
Prepared Via the Reduction/Oxidation Procedure.

A solution of lithium aluminum hydride in tetrahydrofuran (0.229 mL of 1.0 M; 0.229 mmol; 0.6 eq.) was added to a cooled (−78° C.), stirred solution of Intermediate 9 (220 mg; 0.382 mmol) in toluene (4.2 mL) via syringe under a nitrogen atmosphere. Vigorous bubbling was observed. The resulting solution was stirred at −78° C. for 2 hours, and the reaction was quenched with the successive addition of methanol (50 μL), 15% aqueous sodium hydroxide (50 μL), and additional water (200 μL). The resulting mixture was allowed to warm to room temperature, then stirred for 30 minutes and next diluted with ether (8 mL) and dried over $Na_2SO_4$. Filtration and concentration of the filtrate in vacuo provided the alcohol (with some aldehyde present) as a semisolid (242 mg). This material was used immediately without further purification.

To a cooled (−78° C.), stirred solution of oxalyl chloride in dichloromethane (95 μL of 2.0 M; 0.19 mmol; 0.5 eq.) in additional dichloromethane (0.40 mL) was added dimethylsulfoxide (160 μL; 0.38 mmol; 1.0 eq.) via syringe under a nitrogen atmosphere. Vigorous bubbling was observed. After stirring at −78° C. for 20 minutes, a solution of the crude alcohol in dichloromethane (0.6 mL) was added via cannulae. The resulting yellow solution was stirred at −78° C. for 20 minutes, then triethylamine (119 μL; 0.85 mmol; 2.2 eq.) was added via syringe. The resulting reaction mixture was stirred at −78° C. for 20 minutes, then warmed to room temperature and stirred for an additional 1 hour. The reaction mixture next was quenched by the addition of brine (10 mL) and was extracted with dichloromethane (2×10 mL). The combined organic layers were dried over $Na_2SO_4$, filtered, and concentrated in vacuo to provide the crude aldehyde. Purification by flash silica gel chromatography (20% ethyl acetate in hexanes) provided the named aldehyde as a clear, colorless oil (101 mg; 63% for two steps).

$^1$H NMR ($CDCl_3$, 400 MHz): δ 9.68 (s, 1H), 7.57 (d, 1H), 7.41–7.21 (m, 6H), 6.94 (dd, 1H), 4.87 (p, 1H), 3.89 (t, 1H), 3.81 (d, 1H), 3.68 (d, 1H), 3.26–3.20 (m, 2H), 3.01–2.92 (m, 3H), 2.48 (d, 1H), 2.22–2.08 (m, 4H), 2.01–1.92 (m, 2H), 1.78–1.71 (m, 2H), 1.37 (t, 3H), 0.76 (s, 3H).

PREPARATION OF EXAMPLES 1 AND 2

Prepared by the Grignard Addition Procedure.

A solution of methyl magnesium iodide in ether (184 μL of 3.0 M; 0.55 mmol; 3 eq.) was added to a cooled (0° C.), stirred solution of Intermediate 10 (76.8 mg; 0.185 mmol) in dry ether (2.8 mL) via syringe under a nitrogen atmosphere. After stirring at 0° C. for 15 minutes, the reaction mixture was allowed to warm to room temperature and stirred for 2 hours. The reaction mixture then was carefully quenched with saturated aqueous ammonium chloride (10 mL) and extracted with ethyl acetate (3×10 mL). The combined organic portions were washed with brine, dried over $Na_2SO_4$, filtered, and concentrated in vacuo to give an oil. Purification via flash silica gel chromatography (1.5:2.5:0.6 EtOAc:hexanes:MeOH) provided the less polar diastereomer (22 mg; 27%) and the more polar diastereomer (30 mg; 38%) as a colorless oil.

EXAMPLE 1

(1S)-1-[(3S,4S)-4-(1-Cyclopentyl-3-ethyl(1H-indazol-6-yl))-3-methyl-1-benzylpyrrolidin-3-yl]ethan-1-ol Less Polar Diastereomer.

$^1$H NMR (CDCl$_3$, 400 MHz): δ 7.58 (d, 1H), 7.40–7.17 (m, 6H), 6.99 (dd, 1H), 4.88 (c, 1H), 3.80–3.65 (m, 4H), 3.47 (t, 1H), 3.05 (d, 1H), 2.96 (q, 2H), 2.66 (t, 1H), 2.48 (d, 1H), 2.23–2.05 (m, 4H), 2.01–1.91 (m, 2H), 1.79–1.70 (m, 2H), 1.37 (t, 3H), 1.15 (d, 3H), 0.56 (s, 3H). LRMS (Electrospray, positive): Da/e 432.4 (m+1).

EXAMPLE 2

(1R)-1-[(3S,4S)-4-(1-Cyclopentyl-3-ethyl(1H-indazol-6-yl))-3-methyl-1-benzylpyrrolidin-3-yl]ethan-1-ol More Polar Diastereomer.

$^1$H NMR (CDCl$_3$, 400 MHz): δ 7.57 (d, 1H), 7.38–7.21 (m, 6H), 6.99 (dd, 1H), 4.83 (c, 1H), 3.83–3.65 (m, 5H), 3.36 (t, 1H), 3.17 (d, 1H), 2.97 (q, 2H), 2.74 (t, 1H), 2.23–2.02 (m, 4H), 2.00–1.93 (m, 2H), 1.79–1.69 (m, 2H), 1.37 (t, 3H), 1.16 (d, 3H), 0.52 (s, 3H). LRMS (Electrospray, positive): Da/e 432.4 (m+1).

PREPARATION OF EXAMPLE 3

[(3S,4S)-4-(1-Cyclopentyl-3-ethyl(1H-indazol-6-yl))-3-methyl-1-benzylpyrrolidin-3-yl]methan-1-ol Prepared Via the Hydride Reduction Procedure.

To a cooled (0° C.), stirred solution of Intermediate 10 (38.8 mg; 0.0844 mmol) dissolved in anhydrous tetrahydrofuran (0.8 mL) was added lithium aluminum hydride (84.4 μL; 1.0 M in THF; 0.084 mmol; 1.0 eq). After an initial exotherm, the reaction mixture was allowed to warm to room temperature over 1 hour. Aqueous 1N hydrocloric acid (1 mL) was added to the reaction mixture, and stirring was continued for an additional 5 minutes. The reaction mixture then was basified with 1M NaOH to pH=8. The aqueous layer was extracted with ethyl acetate (2×10 mL), and the combined organic layers were washed with brine (10 mL), then dried over $Na_2SO_4$, and concentrated in vacuo, to yield the named alcohol (31 mg; 88%).

$^1$H NMR (CDCl$_3$, 400 MHz) δ: 7.59 (d, 1H), 7.39–7.28 (m, 6H), 6.98 (d, 1H), 3.58–2.80 (m, 8H), 4.04–3.92 (m, 3H), 2.76 (t, 1H), 2.45 (d, 1H), 2.25–1.66 (m, 8H), 1.37 (t, 3H). LRMS (Electrospray, positive): Da/e 418.3 (m+1).

INTERMEDIATE 11

Preparation of [(3S,4S)-4-(1-Cyclopentyl-3-ethyl(1H-indazol-6-yl))-3-methylpyrrolidin-3-yl]methan-1-ol (Free Pyrrolidine)

Prepared Via the Palladium on Carbon Mediated Hydrogenation Procedure.

To a stirred solution of Example 3 (25.5 mg; 0.0611 mmol) in 190 proof ethanol (2.0 mL) was added 10% Pd/C (5 mg; 20 wt. % catalyst). Hydrogen was vigorously bubbled through the solution for 5 minutes. The reaction was allowed to stir at room temperature for 2 hours, then the catalyst was removed by filtration through celite. The solvent then was removed in vacuo to provide the named pyrrolidine (14 mg; 71%).

$^1$H NMR (CDCl$_3$, 400 MHz) δ: 7.59 (d, 1H), 7.20 (d, 1H), 6.92 (d, 1H), 4.92 (c, 1H), 3.82 (m, 1H), 3.14–2.95 (m, 3H), 3.42 (d, 0.5H), 3.36 (d, 0.5H), 3.01 (q, 2H), 2.20–2.08 (m, 4H), 2.00–1.90 (m, 2H), 1.79–1.62 (m, 2H), 1.40 (t, 3H), 0.78 (s, 3H). LRMS (Electrospray, positive): Da/e 328.4 (m+1).

EXAMPLE 4

Preparation of Methyl (3S,4S)-4-(1-cyclopentyl-3-ethyl(1H-indazol-6-yl))-3-(hydroxymethyl)-3-methyl Pyrrolidine Carboxylate Prepared Via the Hunig's Base Mediated Acylation Procedure.

To a cooled (0° C.), stirred solution of Intermediate 11 (14.2 mg; 0.043 mmol) in dry dichloromethane (1.0 mL) was added diisopropylethylamine (5.6 mg; 0.043 mmol; 1.0 eq). Methyl chloroformate (4.1 mg; 0.043 mmol; 1.0 eq) was added dropwise, and the reaction was allowed to warm to room temperature overnight (14 hours). The reaction then was concentrated in vacuo and diluted with ethyl acetate (1.5 mL). The organic phase was washed with brine (2×10 mL), dried over $Na_2SO_4$, and concentrated in vacuo. The crude oil was purified by silica flash chromatography (15% ethyl acetate in hexanes) and yielded Example 4 (8.9 mg; 53%).

$^1$H NMR (CDCl$_3$, 400 MHz; mixture of rotomers): δ 7.61 (d, 1H), 7.18 (d, 1H), 6.92 (d, 1H), 4.88 (c, 1H), 3.96–3.71 (m, 4H), 3.65–3.49 (m, 3H), 3.40 (d, 0.5H), 3.32 (d, 0.5H), 2.97 (q, 2H), 2.20–2.08 (m, 4H), 2.00–1.90 (m, 2H), 1.78–1.63 (m, 2H), 1.38 (t, 3H), 0.78 (s, 3H). LRMS (Electrospray, positive): Da/e 386.4 (m+1).

The compounds of structural formula (II) were tested for an ability to inhibit PDE4. The ability of a compound to inhibit PDE4 activity is related to the IC$_{50}$ value for the compound, i.e., the concentration of inhibitor required for 50% inhibition of enzyme activity. The IC$_{50}$ value for compounds of structural formula (II) were determined using recombinant human PDE4.

The compounds of the present invention typically exhibit an IC$_{50}$ value against recombinant human PDE4 of less than about 100 μM, and preferably less than about 50 μM, and more preferably less than about 25 μm. The compounds of the present invention typically exhibit an IC$_{50}$ value against recombinant human PDE4 of less than about 1 μM, and often less than about 0.10 μM. To achieve the full advantage of the present invention, a present PDE4 inhibitor has an IC$_{50}$ of about 0.001 μM to about 0.3 μM.

The IC$_{50}$ values for the compounds were determined from concentration-response curves typically using concentrations ranging from 0.1 pM to 500 μM. Tests against other PDE enzymes using standard methodology, as described in Loughney et al., *J. Biol. Chem.*, 271, pp. 796–806 (1996), also showed that compounds of the present invention are highly selective for the cAMP-specific PDE4 enzyme.

The production of recombinant human PDEs and the $IC_{50}$ determinations can be accomplished by well-known methods in the art. Exemplary methods are described as follows:

EXPRESSION OF HUMAN PDEs

Expression in Baculovirus-Infected *Spodoptera fugiperda* (Sf9) Cells

Baculovirus transfer plasmids were constructed using either pBlueBacIII (Invitrogen) or pFastBac (BRL-Gibco). The structure of all plasmids was verified by sequencing across the vector junctions and by fully sequencing all regions generated by PCR. Plasmid pBB-PDE1A3/6 contained the complete open reading frame of PDE1A3 (Loughney et al., *J. Biol. Chem.*, 271, pp. 796–806 (1996)) in pBlueBacIII. Plasmid Hcam3aBB contained the complete open reading frame of PDE1C3 (Loughney et al. (1996)) in pBlueBacIII. Plasmid pBB-PDE3A contained the complete open reading frame of PDE3A (Meacci et al., *Proc. Natl. Acad. Sci., USA*, 89, pp. 3731–3725 (1992)) in pBlueBacIII.

Recombinant virus stocks were produced using either the MaxBac system (Invitrogen) or the FastBac system (Gibco-BRL) according to the manufacturer's protocols. In both cases, expression of recombinant human PDEs in the resultant viruses was driven off the viral polyhedron promoter. when using the MaxBac® system, virus was plaque purified twice in order to insure that no wild type (occ+) virus contaminated the preparation. Protein expression was carried out as follows. Sf9 cells were grown at 27° C. in Grace's Insect culture medium (Gibco-BRL) supplemented with 10% fetal bovine serum, 0.33% TC yeastolate, 0.33% lactalbumin hydrolysate, 4.2 mM $NaHCO_3$, 10 $\mu$g/mL gentamycin, 100 units/mL penicillin, and 100 $\mu$g/mL streptomycin. Exponentially growing cells were infected at a multiplicity of approximately 2 to 3 virus particles per cell and incubated for 48 hours. Cells were collected by centrifugation, washed with nonsupplemented Grace's medium, and Quick-frozen for storage.

Expression in *Saccharomyces Cerevisiae* (Yeast)

Recombinant production of human PDE1B, PDE2, PDE4A, PDE4B, PDE4C, PDE4D, PDE5, and PDE7 was carried out similarly to that described in Example 7 of U.S. Pat. No. 5,702,936, incorporated herein by reference, except that the yeast transformation vector employed, which is derived from the basic ADH2 plasmid described in Price et al., *Methods in Enzymology*, 135, pp. 308–318 (1990), incorporated. yeast ADH2 promoter and terminator sequences and the *Saccharomyces cerevisiae* host was the protease-deficient strain BJ2-54 deposited on Aug. 31, 1998 with the American Type Culture Collection, Manassas, Va., under accession number ATCC 74465. Transformed host cells were grown in 2×SC-leu medium, pH 6.2, with trace metals, and vitamins. After 24 hours, YEP medium-containing glycerol was added to a final concentration of 2×YET/3% glycerol. Approximately 24 hr later, cells were harvested, washed, and stored at −70° C.

HUMAN PHOSPHODIESTERASE PREPARATIONS

Phosphodiesterase Activity Determinations

Phosphodiesterase activity of the preparations was determined as follows. PDE assays utilizing a charcoal separation technique were performed essentially as described in Loughney et al. (1996). In this assay, PDE activity converts [32P]cAMP or [32P]cGMP to the corresponding [32P]5'-AMP or [32P]5'-GMP in proportion to the amount of PDE activity present. The [32P]5'-AMP or [32P]5'-GMP then was quantitatively converted to free [32P]phosphate and unlabeled adenosine or guanosine by the action of snake venom 5'-nucleotidase. Hence, the amount of [32P]phosphate liberated is proportional to enzyme activity. The assay was performed at 30° C. in a 100 $\mu$L reaction mixture containing (final concentrations) 40 mM Tris HCl (pH 8.0), 1 $\mu$M $ZnSO_4$, 5 mM $MgCl_2$, and 0.1 mg/mL bovine serum albumin (BSA) Alternatively, in assays assessing PDE1-specific activity, incubation mixtures further incorporated the use of 0.1 mM CaChe and 10 $\mu$g/mL calmodulin. PDE enzyme was present in quantities that yield<30% total hydrolysis of substrate (linear assay conditions). The assay was initiated by addition of substrate (1 mM [32P]cAMP or cGMP), and the mixture was incubated for 12 minutes. Seventy-five (75) Log of Crotalus atrox venom then was added, and the incubation was continued for 3 minutes (15 minutes total). The reaction was stopped by addition of 200 $\mu$L of activated charcoal (25 mg/mL suspension in 0.1 M $NaH_2PO_4$, pH 4). After centrifugation (750×g for 3 minutes) to sediment the charcoal, a sample of the supernatant was taken for radioactivity determination in a scintillation counter and the PDE activity was calculated.

Inhibitor analyses were performed similarly to the method described in Loughney et al., *J. Biol. Chem.*, 271, pp. 796–806 (1996), except both cGMP and cAMP were used, and substrate concentrations were kept below 32 nM, which is far below the Km of the tested PDEs.

Human PDE4A, 4B, 4C, 4D Preparations
Prepartion of PDE4A from *S. Cerevisiae*

Yeast cells (50 g of yeast strain YI26 harboring HDUN1.46) were thawed at room temperature by mixing with 50 mL of Lysis Buffer (50 mM MOPS pH 7.5, 10 $\mu$M $ZnSO_4$, 2 mM $MgCl_2$, 14.2 mM 2-mercaptoethanol, 5 $\mu$g/mL each of pepstatin, leupeptin, aprotinin, 20 $\mu$g/mL each of calpain inhibitors I and II, and 2 mM benzamidine HCl). Cells were lysed in a French® pressure cell (SLM-Aminco®, Spectronic Instruments) at 100° C. The extract was centrifuged in a Beckman JA-10 rotor at 9,000 rpm for 22 minutes at 4° C. The supernatant was removed and centrifuged in a Beckman TI45 rotor at 36,000 rpm for 45 minutes at 4° C.

PDE4A was precipitated from the high-speed supernatant by the addition of solid ammonium sulfate (0.26 g/mL supernatant) while stirring in an ice bath and maintaining the pH between 7.0 and 7.5. The precipitated proteins containing PDE4A were collected via centrifugation in a Beckman JA-10 rotor at 9,000 rpm for 22 minutes. The precipitate was resuspended in 50 mL of Buffer G (50 mM MOPS pH 7.5, 10 $\mu$M $ZnSO_4$, 5 mM $MgCl_2$, 100 mM NaCl, 14.2 mM 2-mercaptoethanol, 2 mM benzamidine HCl, 5 $\mu$g/mL each of leupeptin, pepstatin, and aprotinin, and 20 $\mu$g/mL each of calpain inhibitors I and II) and passed through a 0.45 $\mu$m filter.

The resuspended sample (50 to 100 mL) was loaded onto a 5×100 cm column of Pharmacia SEPHACRYL® S-300 equilibrated in Buffer G. Enzyme activity was eluted at a flow rate of 2 mL/min and pooled for later fractionation.

The PDE4A isolated from gel filtration chromatography was applied to a 1.6×20 cm column of Sigma Cibacron Blue Agarose-type 300 (10 mL) equilibrated in Buffer A (50 mM MOPS pH 7.5, 10 $\mu$M $ZnSO_4$, 5 mM $MgCl_2$, 14.2 mM 2-mercaptoethanol, and 100 mM benzamidine HCl). The column was washed in succession with 50 to 100 mL of Buffer A, 20 to 30 mL of Buffer A containing 20 mM 5'-AMP, 50 to 100 mL of Buffer A containing 1.5 M NaCl, and 10 to 20 mL of Buffer C (50 mM Tris HCl pH 8, 10 $\mu$M ZnSO$_4$, 14.2 mM 2-mercaptoethanol, and 2 mM benzamidine HCl). The enzyme was eluted with 20 to 30 mL of Buffer C containing 20 mM cAMP.

The PDE activity peak was pooled, and precipitated with ammonium sulfate (0.33 g/mL enzyme pool) to remove excess cyclic nucleotlide. The precipitated proteins were resuspended in Buffer X (25 mM MOPS pH 7.5, 5 MM ZnSO$_4$, 50 mM NaCl, 1 mM DTT, and 1 mM benzamidine HCl), and desalted via gel filtration on a Pharmacia PD-10® column per manufacturer's instructions. The enzyme was quick-frozen in a dry ice/ethanol bath and stored at −70° C.

The resultant preparations were about >80% pure by SDS-PAGE. These preparations had specific activities of about 10 to 40 $\mu$mol cAMP hydrolyzed per minute per milligram protein.

Preparation of PDE4B from *S. Cerevisiae*

Yeast cells (150 g of yeast strain YI23 harboring HDUN2.32) were thawed by mixing with 100 mL glass beads (0.5 mM, acid washed) and 150 mL Lysis Buffer (50 mM MOPS pH 7.2, 2 mM EDTA, 2 mM EGTA, 1 mM DTT, 2 mM benzamidine HCl, 5 $\mu$g/mL each of pepstatin, leupeptin, aprotinin, calpain inhibitors I and II) at room temperature. The mixture was cooled to 4° C., transferred to a Bead-Beater®, and the cells lysed by rapid mixing for 6 cycles of 30 seconds each. The homogenate was centrifuged for 22 minutes in a Beckman J2-21M centrifuge using a JA-10 rotor at 9,000 rpm and 4° C. The supernatant was recovered and centrifuged in a Beckman XL-80 ultra-centrifuge using a TI45 rotor at 36,000 rpm for 45 minutes at 4° C. The supernatant was recovered and PDE4B was precipitated by the addition of sold ammonium sulfate (0.26 g/mL supernatant) while stirring in an ice bath and maintaining the pH between 7.0 and 7.5. This mixture was then centrifuged for 22 minutes in a Beckman J2 centrifuge using a JA-10 rotor at 9,000 rpm (12,000×g). The supernatant was discarded and the pellet was dissolved in 200 mL of Buffer A (50 mM MOPS pH 7.5, 5 mM MgCl, 1 mM DTT, 1 mM benzamidine HCl, and 5 $\mu$g/mL each of leupeptin, pepstatin, and aprotinin). The pH and conductivity were corrected to 7.5 and 15–20 mS, respectively.

The resuspended sample was loaded onto a 1.6×200 cm column (25 mL) of Sigma Cibacron Blue Agarose-type 300 equilibrated in Buffer A. The sample was cycled through the column 4 to 6 times over the course of 12 hours. The column was washed in succession with 125 to 250 mL of Buffer A, 125 to 250 mL of Buffer A containing 1.5 M NaCl, and 25 to 50 mL of Buffer A. The enzyme was eluted with 50 to 75 mL of Buffer E (50 mM Tris HCl pH 8, 2 mM EDTA, 2 mM EGTA, 1 mM DTT, 2 mM benzamidine HCl, and 20 mM cAMP) and 50 to 75 mL of Buffer E containing 1 M NaCl. The PDE activity peak was pooled, and precipitated with ammonium sulfate (0.4 g/mL enzyme pool) to remove excess cyclic nucleotide. The precipitated proteins were resuspended in Buffer X (25 mM MOPS pH 7.5, 5 $\mu$M ZnSO$_4$, 50 mM NaCl, 1 mM DTT, and 1 mM benzamidine HCl) and desalted via gel filtration on a Pharmacia PD-10® column per manufacturer's instructions. The enzyme pool was dialyzed overnight against Buffer X containing 50% glycerol. This enzyme was quick-frozen in a dry ice/ethanol bath and stored at −70° C.

The resultant preparations were about >90% pure by SDS-PAGE. These preparations had specific activities of about 10 to 50 $\mu$mol cAMP hydrolyzed per minute per milligram protein.

Preparation of PDE4C from *S. Cerevisiae*

Yeast cells (150 g of yeast strain YI30 harboring HDUN3.48) were thawed by mixing with 100 mL glass beads (0.5 mM, acid washed) and 150 mL Lysis Buffer (50 mM MOPS pH 7.2, 2 mM EDTA, 2 mM EGTA, 1 mM DTT, 2 mM benzamidine HCl, 5 $\mu$g/mL each of pepstatin, leupeptin, aprotinin, calpain inhibitors I and II) at room temperature. The mixture was cooled to 4° C., transferred to a BEAD-BEATER®, and the cells lysed by rapid mixing for 6 cycles of 30 sec each. The homogenate was centrifuged for 22 minutes in a Beckman J2-21M centrifuge using a JA-10 rotor at 9,000 rpm and 4° C. The supernatant was recovered and centrifuged in a Beckman XL-80 ultra-centrifuge using a TI45 rotor at 36,000 rpm for 45 minutes at 4° C.

The supernatant was recovered and PDE4C was precipitated by the addition of solid ammonium sulfate (0.26 g/mL supernatant) while stirring in an ice bath and maintaining the pH between 7.0 and 7.5. Thirty minutes later, this mixture was centrifuged for 22 minutes in a Beckman J2 centrifuge using a JA-10 rotor at 9,000 rpm (12,000×g). The supernatant was discarded and the pellet was dissolved in 200 mL of Buffer A (50 mM MOPS pH 7.5, 5 mM MgCl$_2$, 1 mM DTT, 2 mM benzamidine HCl, and 5 $\mu$g/mL each of leupeptin, pepstatin, and aprotinin). The pH and conductivity were corrected to 7.5 and 15–20 mS, respectively.

The resuspended sample was loaded onto a 1.6×20 cm column (25 mL) of Sigma Cibacron Blue Agarose-type 300 equilibrated in Buffer A. The sample was cycled through the column 4 to 6 times over the course of 12 hours. The column was washed in succession with 125 to 250 mL of Buffer A, 125 to 250 mL of Buffer A containing 1.5 M NaCl, and then 25 to 50 mL of Buffer A. The enzyme was eluted with 50 to 75 mL of Buffer E (50 mM Tris HCl pH 8, 2 mM EDTA, 2 mM EGTA, 1 mM DTT, 2 mM benzamidine HCl, and 20 mM cAMP) and 50 to 75 mL of Buffer E containing 1 M NaCl. The PDE4C activity peak was pooled, and precipitated with ammonium sulfate (0.4 g/mL enzyme pool) to remove excess cyclic nucleotide. The precipitated proteins were resuspended in Buffer X (25 mM MOPS pH 7.2, 5 $\mu$M ZnSO$_4$, 50 mM NaCl, 1 mM DTT, and 1 mM benzamidine HCl) and desalted via gel filtration on a Pharmacia PD-10® column per manufacturer's instructions. The enzyme pool was dialyzed overnight against Buffer X containing 50% glycerol. This enzyme was quick-frozen in a dry ice/ethanol bath and stored at −70° C.

The resultant preparations were about >80% pure by SDS-PAGE. These preparations had specific activities of about 10 to 20 $\mu$mol cAMP hydrolyzed per minute per milligram protein.

Preparation of PDE4D from *S. Cerevisiae*

Yeast cells (100 g of yeast strain YI29 harboring HDUN4.11) were thawed by mixing with 150 mL glass beads (0.5 mM, acid washed) and 150 mL Lysis Buffer (50 mM MOPS pH 7.2, 10 $\mu$M ZnSO$_4$, 2 mM MgCl$_2$, 14.2 mM 2-mercaptoethanol, 2 mM benzamidine HCl, 5 $\mu$g/mL each of pepstatin, leupeptin, aprotinin, calpain inhibitors I and II) at room temperature. The mixture was cooled to 4° C., transferred to a Bead-Beater®, and the cells lysed by rapid mixing for 6 cycles of 30 sec each. The homogenate was centrifuged for 22 minutes in a Beckman J2-21M centrifuge using a JA-10 rotor at 9,000 rpm and 4° C. The supernatant was recovered and centrifuged in a Beckman XL-80 ultra-centrifuge using a TI45 rotor at 36,000 rpm for 45 minutes at 4° C. The supernatant was recovered and PDE4D was precipitated by the addition of solid ammonium sulfate (0.33 g/mL supernatant) while stirring in an ice bath and maintaining the pH between 7.0 and 7.5. Thirty minutes later, this mixture was centrifuged for 22 minutes in a Beckman J2 centrifuge using a JA-10 rotor at 9,000 rpm (12,000×g). The supernatant was discarded and the pellet was dissolved in 100 mL of Buffer A (50 mM MOPS pH 7.5, 10 4M $ZnSO_4$, 5 mM $MgCl_2$, 14.2 mM 2-mercaptoethanol, 100 mM benzamidine HCl, and 5 μg/mL each of leupeptin, pepstatin, aprotinin, calpain inhibitor I and II). The pH and conductivity were corrected to 7.5 and 15–20 mS, respectively.

At a flow rate of 0.67 mL/min, the resuspended sample was loaded onto a 1.6×20 cm column (10 mL) of Sigma Cibacron Blue Agarose-type 300 equilibrated in Buffer A. The column was washed and succession with 50 to 100 mL of Buffer A, 20 to 30 mL of Buffer A containing 20 mM 5'-AMP, 50 to 100 mL of Buffer A containing 1.5 M NaCl, and then 10 to 20 mL of Buffer C (50 mM Tris HCl pH 8, 10 μM $ZnSO_4$, 14.2 mM 2-mercaptoethanol, 2 mM benzamidine HCl). The enzyme was eluted with 20 to 30 mL of Buffer C containing 20 mM cAMP.

The PDE4D activity peak was pooled and precipitated with ammonium sulfate (0.4 g/mL enzyme pool) to remove excess cyclic nucleotide. The precipitated proteins were resuspended in Buffer X (25 mM MOPS pH 7.2, 5 μM $ZnSO_4$, 50 mM NaCl, 1 mM DTT, and 1 mM benzamidine HCl) and desalted via gel filtration on a Pharmacia PD-10® column per manufacturer's instructions. The enzyme pool was dialyzed overnight against Buffer X containing 50% glycerol. This enzyme preparation was quick-frozen in a dry ice/ethanol bath and stored at −70° C.

The resultant preparations were about >80% pure by SDS-PAGE. These preparations had specific activities of about 20 to 50 μmol cAMP hydrolyzed per minute per milligram protein.

| Example No. | Structure | Molecular weight | PDE4 $IC_{50}$ (nM) |
|---|---|---|---|
| 1 | 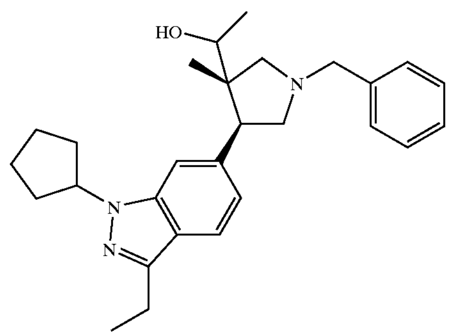 | 431.62 | 315.9 |
| 2 | 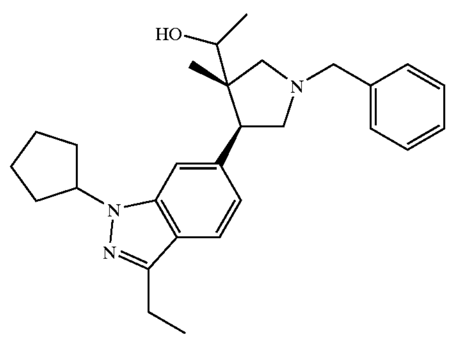 | 431.62 | 87.6 |
| 3 | 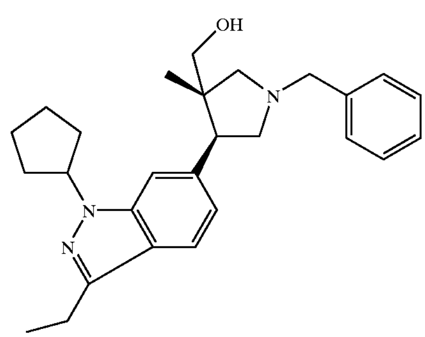 | 417.60 | 6.1 |

-continued

| Example No. | Structure | Molecular weight | PDE4 IC$_{50}$ (nM) |
|---|---|---|---|
| 4 | 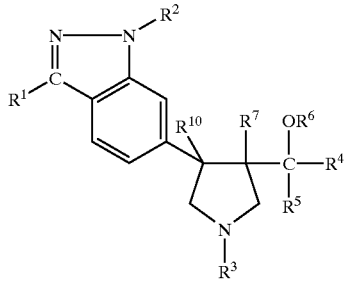 | 385.51 | 79.3 |

The data presented above shows that the present compounds are potent inhibitors of PDE4, e.g., the compounds have an IC$_3$ vs. human recombinant PDE4 of about 0.001 $\mu$M to about 0.3 $\mu$M. Preferred compounds have an IC$_{50}$ of about 100 nM or less, and especially preferred compounds have an IC$_{50}$ of about 50 nM or less.

The compounds of the present invention are useful for selectively inhibiting PDE4 activity in a mammal, without exhibiting the adverse CNS and emetic effects associated with prior PDE4 inhibitors.

Obviously, many modifications and variations of the invention as hereinbefore set forth can be made without departing from the spirit and scope thereof and, therefore, only such limitations should be imposed as are indicated by the appended claims.

What is claimed is:

1. A compound having the formula

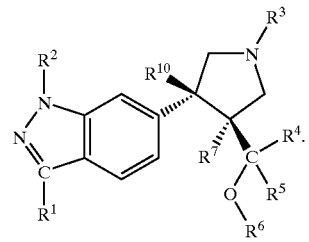

wherein R$^1$ is hydrogen, lower alkyl, bridged alkyl, aryl, heteroaryl, cycloalkyl, a 5- or 6-membered saturated heterocyclic, C$_{1-3}$alkylenecycloalkyl, aryl- or heteroaryl-substituted propargyl, aryl- or heteroaryl-substituted allyl, or halocycloalkyl;

R$^2$ is hydrogen, lower alkyl, bridged alkyl, cycloalkyl, haloalkyl, halocycloalkyl, C$_{1-3}$alkylenecycloalkyl, a 5- or 6-membered saturated heterocycle, aryl, heteroaryl, aralkyl, alkaryl, heteroaralkyl, or heteroalkaryl;

R$^3$ is morpholinyl or piperizinyl;

R$^4$ is hydrogen, lower alkyl, haloalkyl, cycloalkyl, or aryl;

R$^5$ is lower alkyl, alkynyl, haloalkyl, cycloalkyl, or aryl;

R$^6$ is hydrogen, lower alkyl, or C(=O)R$^7$;

R$^7$ is lower alkyl, branched or unbranched, or aryl, either optionally substituted with one or more of RO$^8$, NR$^8$R$^9$, or SR$^8$; and R$^8$ and R$^9$, same or different, are selected from the group consisting of hydrogen, lower alkyl, cycloalkyl, aryl, heteroaryl, alkaryl, heteroaralkyl, heteroalkaryl, and aralkyl, or R$^8$ and R$^9$ together form a 4-membered to 7-membered ring;

R$^{10}$ is hydrogen, alkyl, haloalkyl, cycloalkyl, aryl, C(=O)alkyl, C(=O)cycloalkyl, C(=O)aryl, C(=O)Oalkyl, C(=O)Ocycloalkyl, C(=O)aryl, CH$_2$OH, CH$_2$Oalkyl, CHO, CN, NO$_2$, or SO$_2$R$^{11}$; and R$^{11}$ is alkyl, cycloalkyl, trifluoromethyl, aryl, aralkyl, or NR$^8$R$^9$.

2. The compound of claim 1 having the structure:

3. The compound of claim 1 wherein R$^1$ is selected from the group consisting of hydrogen, alkyl, cycloalkyl, C$_{1-3}$alkylenecycloalkyl, halocycloalkyl, aryl, and heteroaryl.

4. The compound of claim 1 wherein R$^2$ is selected from the group consisting of alkyl, cycloalkyl, aryl, and heteroaryl.

5. The compound of claim 1 wherein R$^5$ is hydrogen or methyl.

6. The compound of claim 1 wherein R$^6$ is selected from the group consisting of hydrogen, acetyl, and benzoyl.

7. The compound of claim 1 wherein R$^7$ is methyl.

8. The compound of claim 1 wherein R$^1$ is selected from the group consisting of cyclopentyl, tetrahydrofuryl, indanyl, norbornyl, phenthyl, and phenylbuty; R$^2$ is selected from the group consisting of hydrogen, ethyl, methyl, and difluoromethyl; R$^4$ is hydrogen; R$^5$ is hydrogen or methyl; R$^6$ is hydrogen; R$^7$ is methyl; and R$^{10}$ is hydrogen.

9. The compound of claim 1 having an IC$_{50}$ vs. human recombinant PDE4 of about 0.001 $\mu$M to about 0.3 $\mu$M.

10. The compound of claim 1 having an IC$_{50}$ vs. human recombinant PDE4 of about 100×10$^{-9}$ M or less.

11. The compound of claim 1 having an IC$_{50}$ vs. human recombinant PDE4 of about 50×10$^{-9}$ M or less.

12. A pharmaceutical composition comprising a compound of claim 1 and a pharmaceutically acceptable carrier.

13. The composition of claim 12 further comprising an antiinflammatory therapeutic agent selected from the group consisting of etanercept and infliximab.

14. A method of treating a mammal having a condition where inhibition of a cAMP-specific PDE is of therapeutic benefit, said method comprising administering to said mammal a therapeutically effective amount of a compound of claim 1.

15. A method of increasing cAMP levels in a mammal comprising administering to said mammal an effective amount of a compound of claim 1.

16. A method of treating a mammal having a condition where inhibition of a cAMP-specific PDE is of a therapeutic benefit comprising administering to said mammal an effective amount of a pharmaceutical composition comprising a compound of claim 1 and a pharmaceutically acceptable carrier.

17. The method of claim 16 wherein the condition is dermititis.

18. The method of claim 16 wherein the condition is rheumatoid arthritis, osteoarthritis, gouty arthritis, or spondylitis.

19. The method of claim 16 wherein the condition is thyroid-associated ophthalmopathy, Behcet disease, sepsis, septic shock, endotoxic shock, gram negative sepsis, gram positive sepsis, toxic shock syndrome, allergic conjunctivitis, vernal conjunctivitis, or eosinophilic granuloma.

20. The method of claim 16 wherein the condition is asthma, chronic bronchitis, allergic rhinitis, adult respiratory distress syndrome, chronic pulmonary inflammatory disease, chronic obstructive pulmonary disease, silicosis, or pulmonary sarcoidosis.

21. The method of claim 16 wherein the condition is reperfusion injury of the myocardium, brain or extremities as a brain or spinal cord injury due to trauma.

22. The method of claim 16 wherein the condition is a fibrosis, keloid formation, or scar tissue formation.

23. The method of claim 16 wherein the condition is systemic lupus erythematosus, a transplant rejection disorder, a graft vs. host reaction, or an allograft rejection.

24. The method of claim 16 wherein the condition is chronic glomerulonephritis, an inflammatory bowel disease, Crohn's disease, or ulcerative colitis.

25. The method of claim 16 wherein the condition is proliferative lymphocytic disease or a leukemia.

26. The method of claim 16 wherein the condition is an inflammatory dermatosis, atopic dermatitis, psoriasis, or urticaria.

27. The method of claim 16 wherein the condition is a cardiomyopathy, congestive heart failure, atherosclerosis, pyrexia, cachexia, cachexia secondary to infection or malignancy, cachexia secondary to acquired immune deficiency syndrome, ARC, cerebral malaria, osteoporosis, a bone resorption disease, fever and myalgias due to infection, diabetes insipidus, a central nervous system disorder, depression, multi-infarct dementia, an anxiety or stress response, cerebral ischemia, tardive dyskinesia, Parkinson's disease, and premenstrual syndrome.

28. The method of claim 16 wherein the mammal exhibits an emetic response less severe than an emetic response exhibited by the mammal after administration of a therapeutically equivalent amount of rolipram.

29. The method of claim 16 wherein the mammal is free of an emetic response.

30. The method of claim 16 wherein the mammal exhibits adverse central nervous system side effects less severe than adverse central nervous system side effects exhibited by the mammal after administration of a therapeutically equivalent amount of rolipram, said adverse central nervous system side effects selected from the group consisting of retching, vomiting, and sedation.

31. The method of claim 16 wherein the mammal is free of adverse central nervous system side effects selected from the group consisting of retching, vomiting, and sedation.

32. A method of reducing TNFα levels in a mammal comprising administering to said mammal therapeutically effective amount of a compound of claim 1.

33. A method of suppressing inflammatory cell activation in a mammal comprising administering to said mammal a therapeutically effective amount of a compound of claim 1.

34. A method of inhibiting PDE4 function in a mammal comprising administering to said mammal a therapeutically effective amount of a compound of claim 1.

* * * * *

UNITED STATES PATENT AND TRADEMARK OFFICE
CERTIFICATE OF CORRECTION

PATENT NO. : 6,444,671 B1
DATED : September 3, 2002
INVENTOR(S) : John J. Gaudino It is certified that error appears in the above-identified patent and that said Letters Patent is hereby corrected as shown below:

Column 1,
Line 50, "(51-AMP)" should be -- (5'-AMP) --

Column 2,
Line 21, "is a manor" should be -- is a major --
Line 52, "qouty arthritis," should be -- gouty arthritis, --
Line 53, "ochthalmopathy" should be -- ophthalmopathy --

Column 7,
Line 24, "halocoalkyl" should be -- halocycloalkyl --
Line 25, "having one more" should be -- having one or more --

Column 8,
Line 17, " "amino is defined as –NH. " should be -- "amino" is defined as $-NH_2$. --
Line 35, "$R^4$ is selected" should be -- $R^3$ is selected --

Column 11,
Line 28, "tartraze," should be -- tartrate --

Column 21,
Line 31, "Na, So.," should be -- $Na_2SO_4$ --

Column 23,
Lines 39 and 40, "(269 mg; 0.8 mmol;" should be -- (269 mg; 0.85 mmol; --

Column 25,
Line 40, "4.83 (c, 1H)" should be -- 4.88 (c, 1H) --

Column 27,
Line 20, "USA, 89, pp. 3731-3725" should be -- USA, 89, PP. 3721-3725 --
Line 26, "promoter. when" should be -- promoter. When --
Line 48, "Methods in Enzymology, 135," should be -- Methods in Enzymology, 185, --

Column 28,
Line 13, "0.1 mM CaChe" should be -- 0.1 mM $CaCl_2$ --
Line 18, "(75) log of Crotalus" should be -- (75) $\mu$g of Crotalus --
Line 41, "at 100°C." should be -- at 10°C. --

UNITED STATES PATENT AND TRADEMARK OFFICE
CERTIFICATE OF CORRECTION

PATENT NO.   : 6,444,671 B1
DATED        : September 3, 2002
INVENTOR(S)  : John J. Gaudino It is certified that error appears in the above-identified patent and that said Letters Patent is hereby corrected as shown below:

Column 29,
Line 11, "pH 7.5, 5 MM" should be -- pH 7.5, 5 $\mu$M --

Column 31,
Line 9, "10 4M ZnSO$_4$." should be -- 10 $\mu$M ZnSO$_4$. --
Line 17, "was washed and succession" should be -- was washed in succession --

Signed and Sealed this

Twenty-second Day of April, 2003

JAMES E. ROGAN
*Director of the United States Patent and Trademark Office*